(12) United States Patent
Kondo et al.

(10) Patent No.: US 6,210,603 B1
(45) Date of Patent: Apr. 3, 2001

(54) FLUORINE-SUBSTITUTED BENZENE DERIVATIVE, LIQUID-CRYSTAL COMPOSITION, AND LIQUID-CRYSTAL DISPLAY ELEMENT

(75) Inventors: Tomoyuki Kondo; Kazutoshi Miyazawa; Hiroyuki Takeuchi; Shuichi Matsui; Yasusuke Hisatsune; Fusayuki Takeshita; Etsuo Nakagawa, all of Chiba (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/308,983
(22) PCT Filed: Nov. 27, 1997
(86) PCT No.: PCT/JP97/04331
    § 371 Date: May 28, 1999
    § 102(e) Date: May 28, 1999
(87) PCT Pub. No.: WO98/23564
    PCT Pub. Date: Jun. 4, 1998

(30) Foreign Application Priority Data

Nov. 28, 1996 (JP) .................................................. 8-332768

(51) Int. Cl.⁷ .......................... C09K 19/12; C09K 19/06; C09K 19/34; C07C 19/08; C07C 41/00
(52) U.S. Cl. .................. 252/299.66; 252/299.6; 252/299.61; 252/299.67; 570/144; 568/626; 568/647
(58) Field of Search .................... 252/299.66, 299.6, 252/299.61, 299.67; 570/144; 568/626, 647

(56) References Cited

U.S. PATENT DOCUMENTS

| | | | |
|---|---|---|---|
| 4,405,488 | 9/1983 | Sugimori et al. | 252/299.63 |
| 5,032,313 | 7/1991 | Goto et al. | 252/299.63 |
| 5,273,680 | 12/1993 | Gray et al. | 252/299.66 |
| 5,324,449 | 6/1994 | Kurmeier et al. | 252/299.01 |
| 5,487,845 | 1/1996 | Reiffenrath et al. | 252/299.63 |
| 5,496,499 | * 3/1996 | Poetsch et al. | 252/299.66 |
| 5,536,442 | 7/1996 | Reiffenrath et al. | 252/299.01 |
| 5,571,449 | * 11/1996 | Bartmann et al. | 252/299.6 |
| 5,626,793 | * 5/1997 | Reiffenrath et al. | 252/299.63 |
| 5,641,429 | * 6/1997 | Reiffenrath et al. | 252/299.61 |
| 5,705,095 | * 1/1998 | Bartmann et al. | 252/299.66 |
| 5,718,840 | * 2/1998 | Plach et al. | 252/299.66 |
| 5,730,904 | * 3/1998 | Bartmann et al. | 252/299.63 |
| 5,858,275 | * 1/1999 | Matsui et al. | 252/299.63 |
| 5,861,109 | 1/1999 | Goodby et al. | 252/299.65 |
| 5,872,301 | * 2/1999 | Schlosser et al. | 568/647 |
| 5,932,138 | * 8/1999 | Plach et al. | 252/299.66 |

FOREIGN PATENT DOCUMENTS

| | | |
|---|---|---|
| 0439089 | 7/1991 | (EP) . |
| 2257701 | 1/1993 | (GB) . |
| 1-242542 | 9/1989 | (JP) . |
| 3-503771 | 8/1991 | (JP) . |
| 4-217930 | 8/1992 | (JP) . |
| 8-502499 | 3/1996 | (JP) . |
| 8-511261 | 11/1996 | (JP) . |
| 91/08184 | 6/1991 | (WO) . |

\* cited by examiner

Primary Examiner—C. H. Kelly
(74) Attorney, Agent, or Firm—Wenderoth, Lind & Ponack, L.L.P.

(57) ABSTRACT

Liquid crystalline compounds are provided which have an extremely high voltage holding ratio, altered only slightly by change of temperature, and which have a low threshold voltage and a high Δn. Also provided are liquid crystal compositions containing the liquid crystalline compound; and liquid crystal display devices containing the liquid crystal composition. The liquid crystalline compound is expressed by the general formula (1)

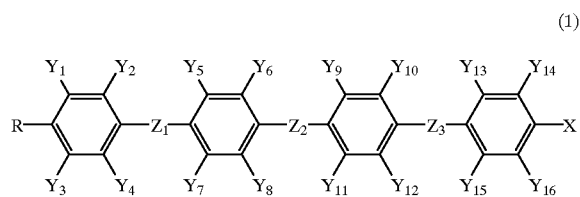

(1)

wherein R, $Y_1$ to $Y_{16}$, X and $Z_1$ to $Z_3$ are defined in claim 1.

11 Claims, No Drawings

FLUORINE-SUBSTITUTED BENZENE DERIVATIVE, LIQUID-CRYSTAL COMPOSITION, AND LIQUID-CRYSTAL DISPLAY ELEMENT

This application is a 371 application of International Application No. PCT/JP97/04331 filed Nov. 27, 1997.

TECHNICAL FIELD

The present invention relates to novel liquid crystalline compounds, liquid crystal compositions, and liquid crystal display devices fabricated by using the liquid crystal composition. More specifically, the invention relates to liquid crystalline compounds having fluorine substituted 1,4-phenylene group, liquid crystal composition comprising the liquid crystalline compound, and liquid crystal display devices fabricated by using the liquid crystal composition.

BACKGROUND ART

Display devices produced by using liquid crystalline compounds (the term "liquid crystalline compound(s)" is used in this specification as a general term for the compounds which exhibit a liquid crystal phase and for the compounds which do not exhibit a liquid crystal phase but are useful as component of liquid crystal compositions) have widely been utilized for the display of watches, tabletop calculators, word processors, or the likes. In recent years, researches on TFT type displays having characteristics such as a high contrast and wide visual angle are extensively conducted.

For liquid crystal compositions used for TFT, physical properties such as voltage holding ratio is high, threshold voltage (Vth) is low, their alteration caused by the change of temperature is small, temperature range of liquid crystal phase is wide, miscibility with other liquid crystal materials is excellent, and viscosity is low have been sought. Further, liquid crystal compositions having a high optical anisotropy (Δn) are useful for increasing response speed.

For these purposes, fluorine containing compounds are suitable. Many researches have been conducted up to now and for example, (1) Japanese Patent Publication No. Sho 63-13411, (2) Japanese Patent Publication No. Sho 63-44132, (3) Laid-open Japanese Patent Publication No. Hei 2-233626, (4) Laid-open PCT Japanese Publication (Tokuhyo) No. Hei 2-501311, (5) Laid-open PCT Japanese Publication No. Hei 3-500413, (6) Laid-open PCT Japanese Publication No. Hei 2-501071, (7) Laid-open PCT Japanese Publication No. Hei 3-503711, (8) Laid-open Japanese Patent Publication No. Hei 4-217930, (9) Laid-open PCT Japanese Publication No. Hei 4-501575, (10) Laid-open PCT Japanese Publication No. Hei 6-504032, and (11) EP-439089 are published.

A part of the compounds of the present invention are formally included in the general formula disclosed in the publications (6) to (11) mentioned above. However, data such as physical property values of the compounds which correspond to the ones of the present invention are not disclosed at all and their specific characteristics are not specifically described in any one of the publications mentioned above. Accordingly, those publications have not suggested the present invention.

DISCLOSURE OF THE INVENTION

In view of the required characteristics described above in relation to liquid crystal compositions for TFT, an object of the present invention is to provide (a) liquid crystalline compounds which have an extremely high voltage holding ratio, are small in its alteration caused by the change of temperature, have a low threshold voltage and high Δn; (b) liquid crystal compositions comprising the compound; and (c) liquid crystal display devices fabricated by using the liquid crystal composition.

As a result of a diligent investigation by the present inventors, it has been found out that the liquid crystalline compounds expressed by the following general formula (1) have intended properties, leading to the accomplishment of the present invention:

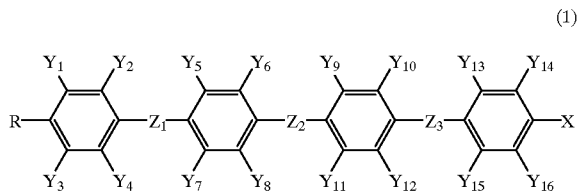

(1)

wherein R represents an alkyl group having 1 to 20 carbon atoms in which alkyl group any not-adjacent methylene group ($-CH_2-$) may be replaced by oxygen ($-O-$) atom; $Y_1$ to $Y_{16}$ independently represent hydrogen atom or fluorine atom, but at least three of them are fluorine atoms, provided that in no case three or more hydrogen atoms of one 1,4-phenylene group are replaced by fluorine atom; X represents a halogen atom or an alkyl group having 1 to 20 carbon atoms in which alkyl group any not-adjacent methylene group may be replaced by oxygen atom, and any hydrogen atom in the alkyl group may be replaced by fluorine atom; $Z_1$, $Z_2$, and $Z_3$ independently represent $-(CH_2)_2-$, $-(CH_2)_4-$, $-CH_2O-$, $-OCH_2-$, $-(CH_2)_3O-$, $-O(CH_2)_3-$, or single bond; and any atom which constitutes this compound may be replaced by its isotope; provided that when X=$-OCF_2CF_2H$, $Z_1$=$Z_3$=single bond, and $Z_2$=$-(CH_2)_2-$, in no case $Y_6$=$Y_{10}$=$Y_{12}$F, and $Y_1$ to $Y_5$=$Y_7$ to $Y_9$=$Y_{11}$=$Y_{13}$ to $Y_{16}$=H, $Y_2$=$Y_{10}$=$Y_{12}$=F, and $Y_1$=$Y_3$ to $Y_9$=$Y_{11}$=$Y_{13}$ to $Y_{16}$=H, or $Y_2$=$Y_4$=$Y_{10}$=$Y_{12}$=F, and $Y_1$=$Y_3$=$Y_5$ to $Y_9$=$Y_{11}$=$Y_{13}$ to $Y_{16}$=H.

Compounds expressed by the general formula (1) are classified as follows:

In the following formulas (1a) to (1h), R and X have the same meaning as described above, Za to Zc independently represent $-(CH_2)_2-$, $-(CH_2)_4-$, $-CH_2O-$, $-OCH_2-$, $-(CH_2)_3O-$, or $-O(CH_2)_3-$, and P represents 1,4-phenylene group in which any one or two hydrogen atoms may be replaced by fluorine atom.

 R—P—P—P—P—X (1a)

 R—P—Za—P—P—P—X (1b)

 R—P—P—Zb—P—P—X (1c)

 R—P—P—P—Zc—P—X (1d)

 R—P—Za—P—Zb—P—P—X (1e)

 R—P—Za—P—P—Zc—P—X (1f)

 R—P—P—Zb—P—Zc—P—X (1g)

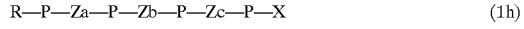 R—P—Za—P—Zb—P—Zc—P—X (1h)

Among these compounds, compounds expressed by one of the formulas (1a) to (1d) are especially preferable for achieving the purpose of the present invention.

Among these formulas, R is a straight chain or branched alkyl group having 1 to 20 carbon atoms. As the straight chain alkyl group, methyl, ethyl, propyl, butyl, pentyl, hexyl, heptyl, decyl, pentadecyl, and icosyl; and as branched alkyl group, isopropyl, sec-butyl, tert-butyl, 2-methyl-butyl, isopentyl, isohexyl, 3-ethyloctyl, and 3,8-dimethyltetradecyl can specifically be mentioned.

In these alkyl groups, any methylene group (—$CH_2$—) may be replaced by oxygen (—O—) unless oxygen atom continues. As examples of alkyl groups in which methylene group is replaced by oxygen, alkoxy groups and alkoxyalkyl groups can be mentioned.

As more specific examples of these groups, alkoxy groups such as methoxy, ethoxy, propoxy, butoxy, pentyloxy, and nonyloxy; alkoxyalkyl groups such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl, and octyloxymethyl can be mentioned.

X represents a halogen atom or an alkyl group having 1 to 20 carbon atoms. In this alkyl group, any methylene group (—$CH_2$—) may be replaced by oxygen (—O—) unless oxygen atom continues, and hydrogen atom in the group may be replaced by fluorine atom. Specifically, the alkyl groups, alkoxy groups, and alkoxyalkyl groups described above can be mentioned as examples.

Further, as fluoroalkyl group, fluoromethyl, difluoromethyl, trifluoromethyl, 1,1,2,2-tetrafluoroethyl, perfluoroethyl, 1,1,2,2-tetrafluoropropyl, 1,1,3,3-tetrafluoropropyl, 2,2,3,3-tetrafluoropropyl, 1,1,2,3-tetrafluoropropyl, 1,2,2,3-tetrafluoropropyl, 1,2,3,3-tetrafluropropyl, 1,1,3,3,3-pentafluoropropyl, 1,1,2,3,3,3-hexafluoropropyl, 1,1,4,4,4-pentafluoro-butyl, 1,2,5,5-tetrafluoropentyl, and perfluoroicosyl;

as fluoroalkoxy group, difluoromethoxy, trifluoromethoxy, 1,1,2,2-tetrafluoroethoxy, perfluoroethoxy, 1,1,2,2-tetrafluoropropoxy, 1,1,3,3-tetrafluoropropoxy, 1,1,3,3,3-pentafluoropropoxy, 1,1,2,3,3,3-hexafluoropropoxy, 1,1,4,4,4-pentafluorobutoxy, and 1,1,2,3,5,5,5-heptafluoropentyloxy; and as alkoxyalkyl group replaced by fluorine, (trifluoromethoxy)fluoromethyl, (1,1,2,2-tetrafluoroethoxy) methyl, 1,2,2,2-tetrafluroethoxy)methyl, (perfluoroethoxy) methyl, (1,1,3,3-tetrafluoropropoxy)methyl, (1,1,3,3,3-pentafluoropropoxy)methyl, (1,1,2,3,3,3-hexafluropropoxy) methyl, (1,1,4,4,4-pentafluorobutoxy)methyl, 2-(1,1,2,2-tetrafluoroethoxy)ethyl, 2-(perfluoroethoxy)ethyl, 2-(1,1,3,3,3-pentafluoropropoxy)ethyl, 2-(1,1,2,3,3,3-hexafluoropropoxy)ethyl, 2-(1,1,2,2-tetrafluroethoxy) propyl, 3-(perfluroethoxy)propyl, 2-(1,1,3,3,3-pentafluoropropoxy)propyl, 2-(1,1,2,3,3,3-hexafluoropropoxy) propyl, 4-(1,1,2,2-tetrafluoroethoxy) butyl, 4-(1,1,2,3,3,3-hexafluoropropoxy)butyl, 5-(1,2,2,2-tetrafluoroethoxy)pentyl, and 5-(1,1,3,3,3-pentafluoropropoxy)pentyl can be mentioned as examples.

Compounds in which the R and/or X described above is an optically active group are particularly useful as chiral dopant.

In the general formula (1), while $Z_1$, $Z_{21}$ and $Z_3$ independently represent —$(CH_2)_2$—, —$(CH_2)_4$—, —$CH_2O$—, —$OCH_2$—, —$(CH_2)_3O$—, —$O(CH_2)_3$—, or single bond, they are preferably —$(CH_2)_2$—, —$(CH_2)_4$—, —$CH_2O$—, —$OCH_2$—, or single bond, and more desirably —$(CH_2)_2$— or single bond.

Compounds of the present invention exhibit a comparatively high phase transition temperature to an isotropic phase.

Compounds of the present invention have a positive and extremely high Δε, and a low threshold voltage when X is a strong polar group such as a halogen atom or $CF_3$, and the compounds exhibit a comparatively low viscosity when the X is a weak polar group such as an alkyl group and alkoxy group.

Whereas some of the compounds of the present invention exhibit a negative Δε value, these compounds are suitable as component of liquid crystal compositions for in-plane switching (IPS) mode and vertical alignment (VA) mode.

Further, an atom which constitutes the compounds expressed by the general formula (1) may be replaced by its isotope. Even in such case, the compounds exhibit characteristics equal to those of the compounds in which any atom is not replaced by the isotope.

By properly selecting these substituents and bonding groups, compounds having desired physical properties can be obtained.

Liquid crystalline compounds of the present invention expressed by the general formula (1) can be manufactured by ordinary methods of organic synthesis, and can conveniently be produced, for example, by the following methods:

scheme 1

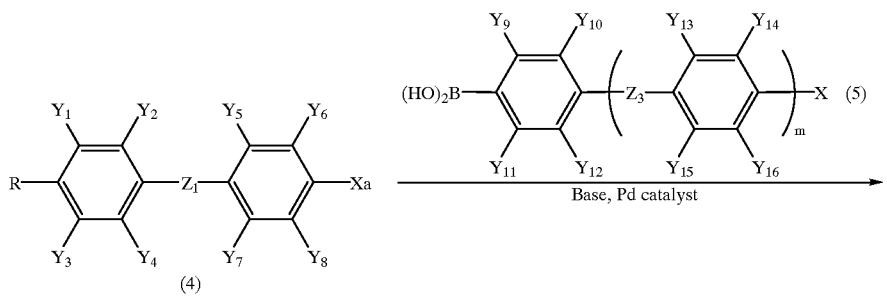

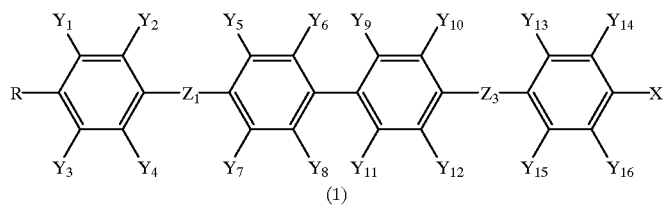
scheme 2
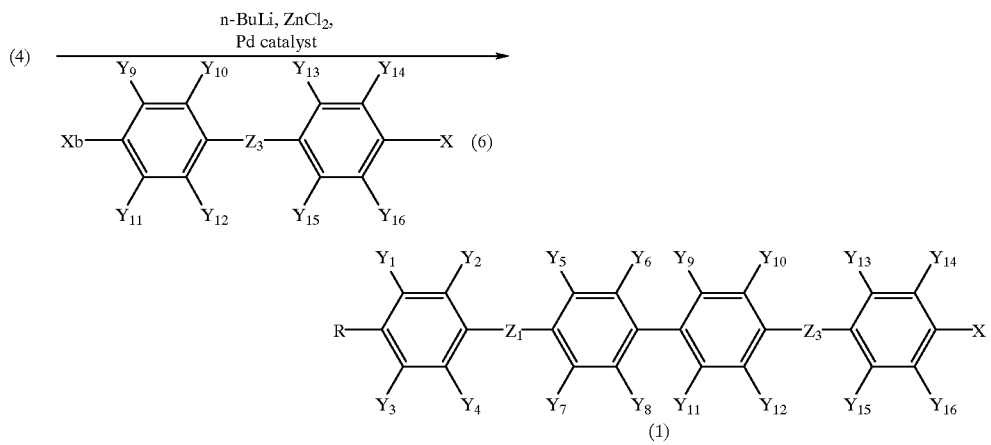
scheme 3
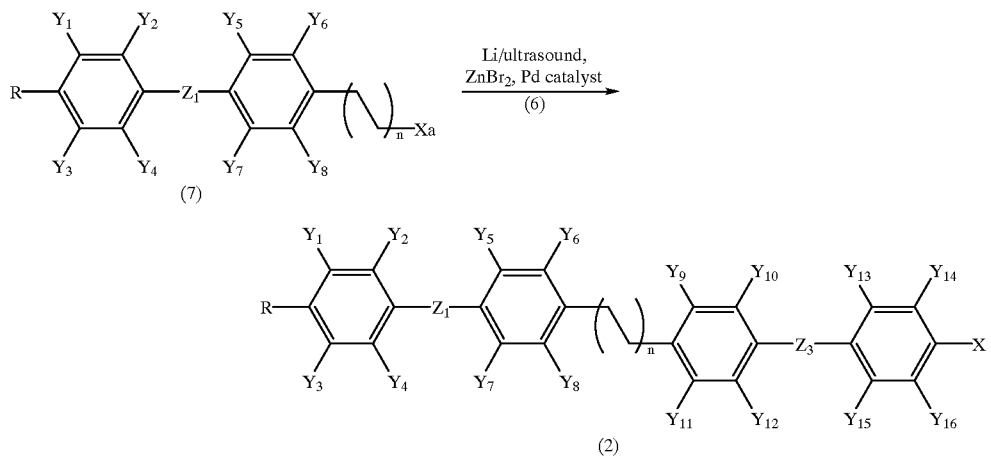
scheme 4
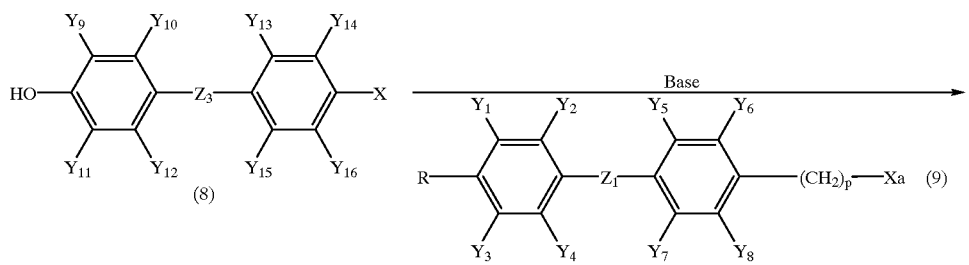

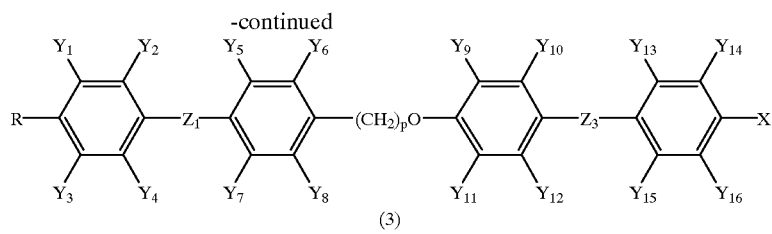

(3)

wherein R, X, $Y_1$ to $Y_{16}$, $Z_1$, $Z_3$, and m have the same meaning as described above, Xa and Xb represent a halogen atom, n is 1 or 2, and p is 1 or 3.

That is, as shown in scheme 1, Compound (1) of the present invention can be produced by reacting Compound (4) with Compound (5) in a mixed solvent of toluene, xylene, or the like, an alcohol such as ethanol, and water in the presence of a base such as $K_2CO_3$ or $Na_2CO_3$, and a catalyst such as palladium carried on carbon (Pd—C), $Pd(PPh_3)_4$, and $PdCl_2(PPh_3)_2$.

Alternatively, as shown in scheme 2, Compound (1) can be produced even by reacting Compound (4) with a lithium compound such as n-BuLi and sec-BuLi, and a zinc compound such as $ZnCl_2$ and $ZnBr_2$, and then reacting with Compound (6).

As shown in scheme 3, Compound (2) of the present invention can be produced by lithiating Compound (7) and then reacting with a zinc compound and Compound (6).

Also, as shown in scheme 4, Compound (3) of the present invention can be produced by reacting Compound (8) with Compound (9) in a solvent such as dimethyl sulfoxide, dimethyl formamide, 1,2-dimethoxyethane, tetrahydrofuran, hexamethylphosphoric triamide, and toluene in the presence of a base such as sodium amide (J. B. Wright et al., Journal of the American Chemical society, 70, 3098 (1948)), potassium carbonate (W. T. Olson et al., Journal of the American Chemical Society, 69, 2451 (1947)), triethyl amine (R. L. Merker et al., The Journal of Organic Chemistry, 26, 5180 (1961)), sodium hydroxide (C. Wilkins, Synthesis, 156 (1973)), potassium hydroxide (J. Rebek et al., The Journal of Organic Chemistry, 44, 1485 (1979)), barium hydroxide (Kawabe et al., The Journal of Organic Chemistry, 37, 4210 (1972)), or sodium hydride (C. J. Stark, Tetrahedron Letters, 22, 2089 (1981), and K. Takai et al., Tetrahedron Letters, 21, 1657 (1980)).

Substituent X can readily be introduced into benzene ring at any stage by using a starting material in which the substituent is introduced in advance, or by using a known method. Some of their specific examples are shown below.

scheme 5

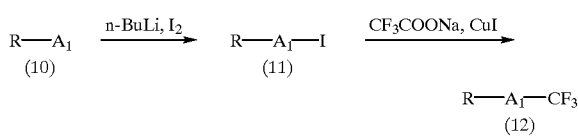

scheme 6

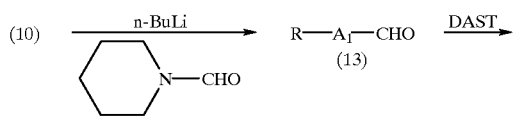

scheme 7

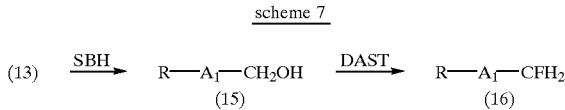

scheme 8

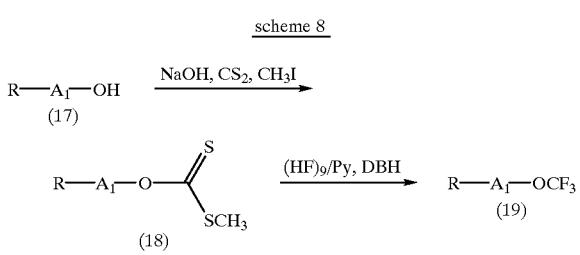

scheme 9

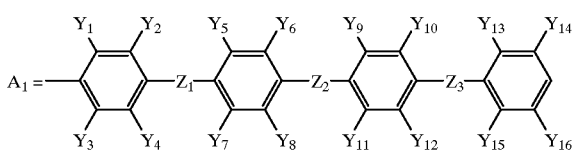

wherein R have the same meaning as described above and Al represents the following group:

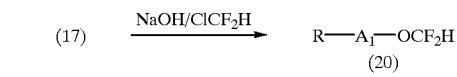

wherein $Y_1$ to $Y_{16}$ and $Z_1$ to $Z_3$ have the same meaning as described above.

That is, as shown in scheme 5, Compound (10) is reacted with a lithium compound such as n-butyl lithium and iodine to convert it into Compound (11). Subsequently, the Compound (11) can be reacted with sodium trifluoroacetate/copper iodide (I) (G. E. Carr et al., Journal of the Chemical Society Perkin Transactions I, 921 (1988)) or methyl fluorosulfonyldifluoroacetate/copper iodide (I) (Q. Y. Chen et al., Journal of the Chemical Society Chemical Communications, 705 (1989)) to produce trifluoromethyl compound (12).

As shown in scheme 6, Compound (10) can be reacted with a lithium compound such as n-butyl lithium, and a formylating agent such as N-formylpiperidine (G. A. Olah et al., Angewandte Chemie International Edition in English, 20, 878 (1981)), N-formylmorpholine (G. A. Olah et al., The Journal of Organic Chemistry, 49, 385 (1984)), and DMF (G. Boss et al., Chemische Berichte, 1199 (1989)) to convert it into Compound (13), and then reacting the compound with a fluorinating agent such as diethylaminosulfur trifluoride (DAST) (W. J. Middleton et al., The Journal of Organic Chemistry, 40, 574 (1975), S. Rozen et al., Tetrahedron Letters, 41, 111 (1985), M. Hudlicky, Organic Reactions, 35, 513 (1988), and P. A. Messina et al., Journal of Fluorine Chemistry, 42, 137 (1989)), and morpholinosulfur trifluoride (K. C, Mange et al., The Journal of Fluorine Chemistry, 43, 405 (1989)) to produce difluoromethyl compound (14).

As shown in scheme 7, Compound (13) can be reduced with a reducing agent such as sodium borohydride (SBH), lithium aluminum hydride, diisobutyl aluminum hydride, and sodium bis(2-methoxyethoxy)aluminum hydride to form Compound (15) and then reacted with a fluorinating agent such as DAST to produce monofluoromethyl compound (16).

As shown in scheme 8, Compound (17) is converted into Compound (18) by the method of Albert et al. (Synthetic Communications, 19, 547 (1989). This compound can be fluorinated by the method of Kurohoshi et al. (Tetrahedron Letters, 33, 29, 4173 (1992) to produce trifluoromethoxy compound (19).

Further, as shown in scheme 9, Compound (17) can be fluorinated in a system of chlorodifluoromethane/sodium hydroxide (Laid-open PCT Japanese Publication No. Hei 3-500413) to produce difluoromethoxy compound (20). Alternatively, it can be produced even by the method of Chen et al. (The Journal of Fluorine Chemistry, 44, 433 (1989).

While halogen compounds and dihydroxyborane derivatives which are staring materials can also be produced by general methods of organic synthesis, they can conveniently be produced, for example, by the following method:

scheme 10

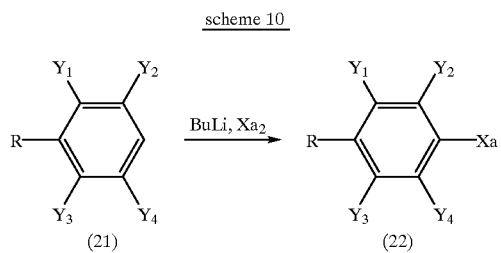

(21) → (22)

scheme 11

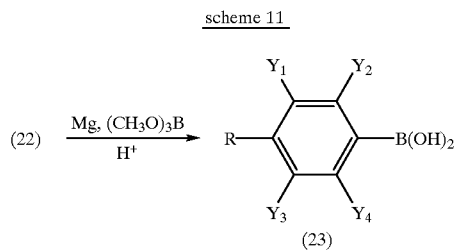

(22) → (23)

wherein R, $Y_1$ to $Y_4$, and Xa have the same meaning as described above.

That is, as shown in scheme 10, halogen compound (22) can be produced by reacting Compound (21) with a lithium compound such as n-BuLi, and iodine, bromine, or the like.

Further, as shown in scheme 11, dihydroxyborane derivative (23) can be produced by reacting a Grignard reagent prepared from compound (22) and magnesium, with a borane derivative such as trimethoxyborane and triisopropyloxyborane, and then hydrolyzing with hydrochloric acid or the like.

Intended compounds of the present invention can be produced by using the reactions described above in combination depending on the properties of the compounds to be produced. Reactions described above are all known in public, and it is needless to say that other known reactions can be used when necessary.

Liquid crystalline compounds of the present invention obtained by such methods have an extremely high voltage holding ratio, are considerably small in its alteration by the change of temperature, and have a low threshold voltage and a high Δn.

Further, these liquid crystalline compounds of the present invention are sufficiently stable chemically and physically under conditions wherein liquid crystal display devices are ordinarily used, and are remarkably excellent as component of nematic liquid crystal compositions.

The compounds of the present invention can suitably used as component even in liquid crystal compositions for TN, STN, TFT, or other display modes.

Liquid crystal compositions of the present invention will be described below.

Liquid crystal compositions of the present invention preferably comprise at least one compound expressed by the general formula (1) in a ratio of 0.1 to 99.9% by weight to develop excellent characteristics, and the ratio is more preferably 1 to 60% by weight.

In more detail, the liquid crystal compositions of the present invention are completed by mixing a compound selected from the group consisting of the compounds expressed by one of the general formulas (2) to (12) depending on the purposes of the liquid crystal compositions to be produced, in addition to a first component comprising at least one compound of the general formula (1).

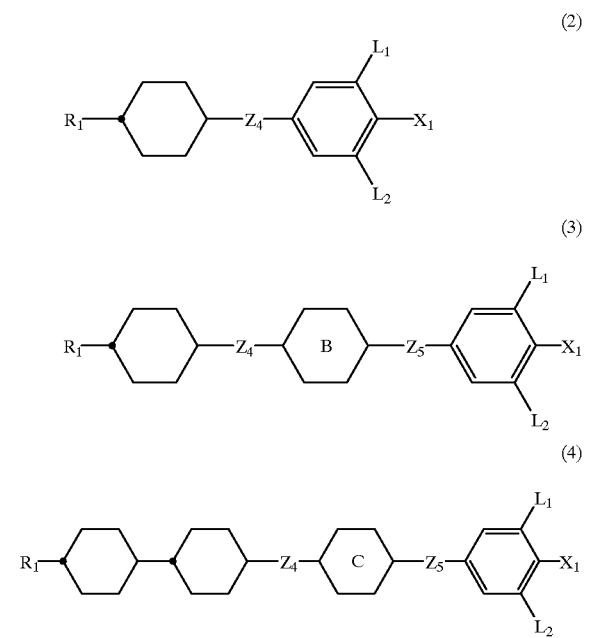

wherein $R_1$ represents an alkyl group having 1 to 10 carbon atoms in which alkyl group any not-adjacent methylene group may be replaced by oxygen atom or —CH=CH—, and any hydrogen atom in the alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently represent hydrogen atom or fluorine atom; $Z_4$ and $Z_5$ independently represent 1,2-ethylene group, 1,4-butylene group, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; ring C represents trans-1,4-cyclohexylene, or 1,4-phenylene in which hydrogen atom may be replaced by fluorine atom; and any atom which constitutes these compounds may be replaced by its isotope, (5)

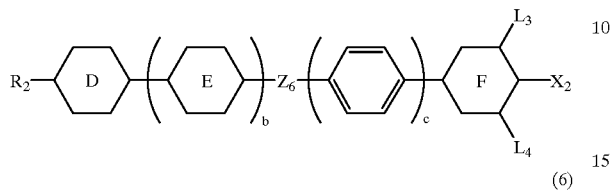

(6)

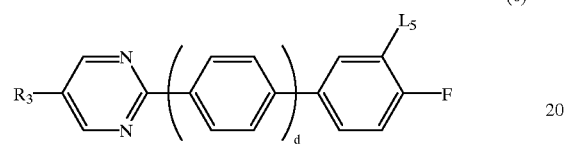

wherein $R_2$ and $R_3$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; $Z_6$ represents 1,2-ethylene group, —COO—, or single bond; $L_3$, $L_4$, and $L_5$ independently represent hydrogen atom or fluorine atom; b, c, and d are independently 0 or 1; and any atom which constitutes these compounds may be replaced by its isotope, (7)

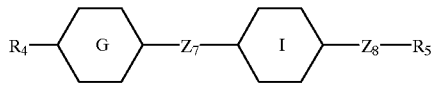

(8)

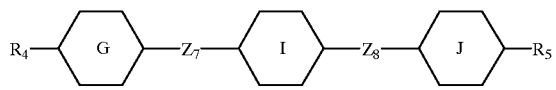

(9)

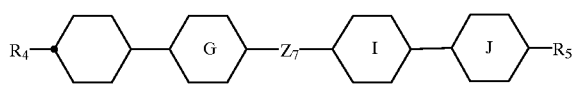

wherein $R_4$ and $R_5$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring G, ring I, and ring J independently represent trans-1,4-cyclohexylene or pyrimidine-2,5-diyl, or 1,4-phenylene in which hydrogen atom may be replaced by fluorine atom; $Z_7$ and $Z_8$ independently represent —C≡C—, —COO—, —CH$_2$CH$_2$—, —CH=CH—, or single bond; and any atom which constitutes these compounds may be replaced by its isotope, (10)

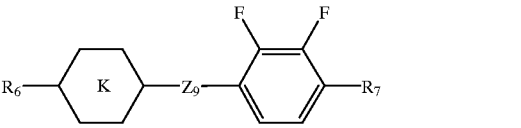

(11)

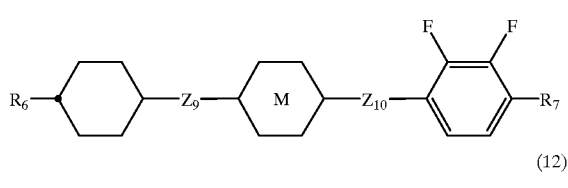

(12)

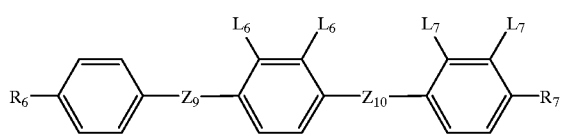

wherein $R_6$ and $R_7$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring K and ring M independently represent trans-1,4-cyclohexylene or 1,4-phenylene; $L_6$ and $L_7$ independently represent hydrogen atom or fluorine atom, but in no case $L_6$ and $L_7$ simultaneously represent hydrogen atom; $Z_9$ and $Z_{10}$ independently represent —CH$_2$CH$_2$—, —COO—, or single bond; and any atom which constitutes these compounds may be replaced by its isotopes.

As the compounds used in the liquid crystal compositions of the present invention and expressed by one of the general formulas (2) to (4), the following compounds can preferably be mentioned:

(2-1)

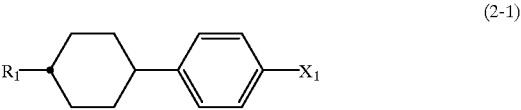

(2-2)

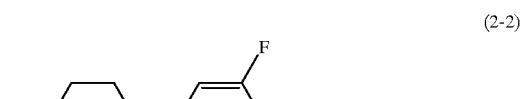

(2-3)

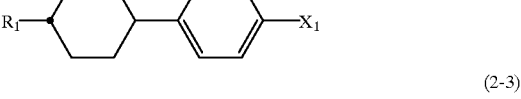

(2-4)

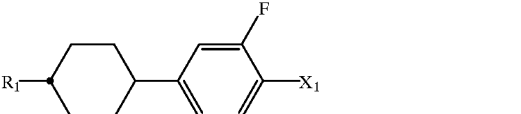

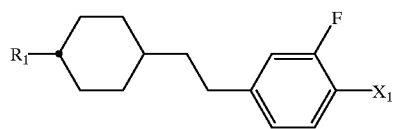
(2-5)
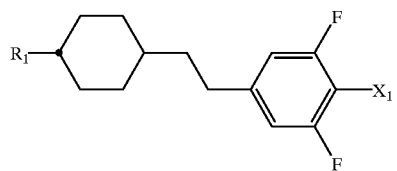
(2-6)
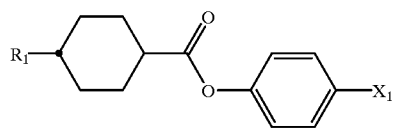
(2-7)
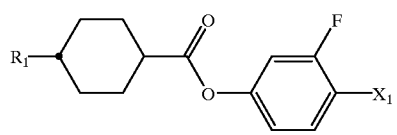
(2-8)
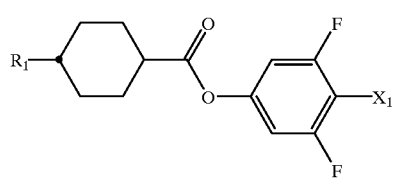
(2-9)
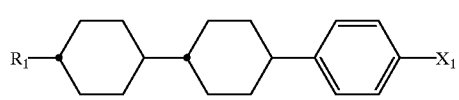
(3-1)
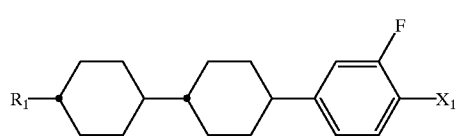
(3-2)
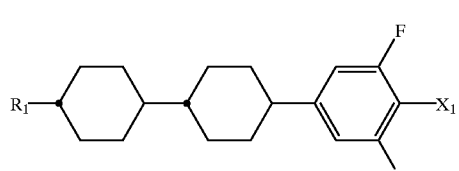
(3-3)
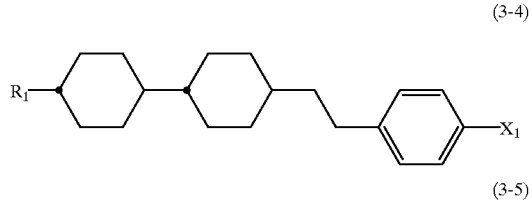
(3-4)
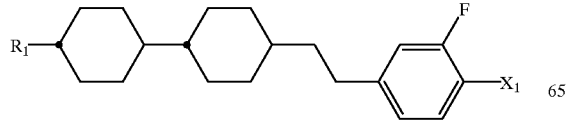
(3-5)
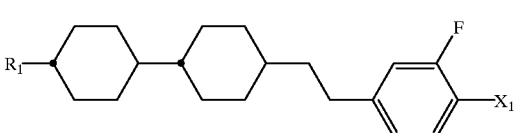
(3-6)
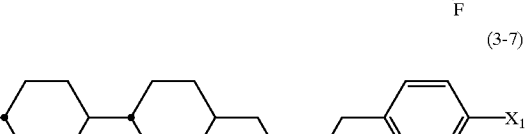
(3-7)
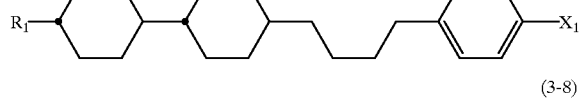
(3-8)
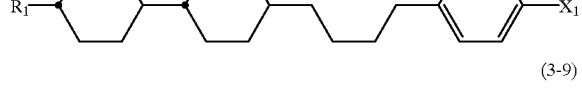
(3-9)
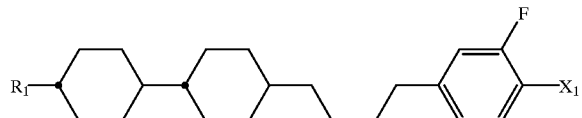
(3-10)
(3-11)
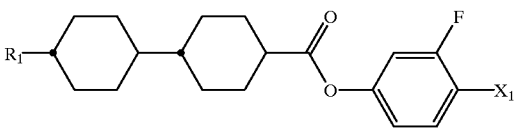
(3-12)
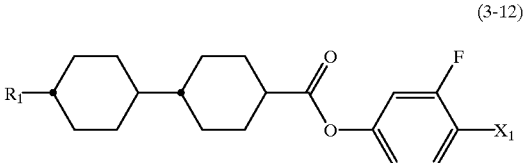
(3-13)
(3-14)
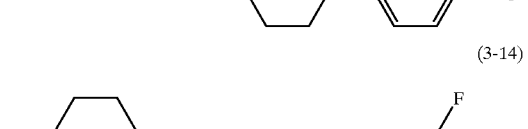
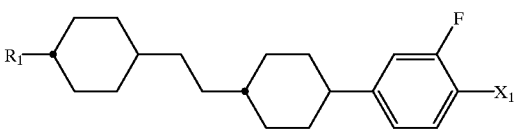

(3-15) 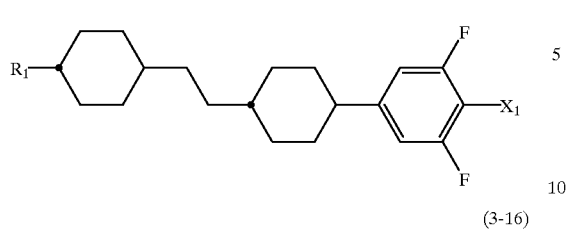
(3-16) 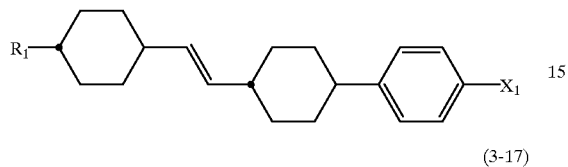
(3-17) 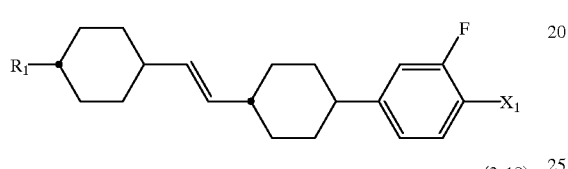
(3-18) 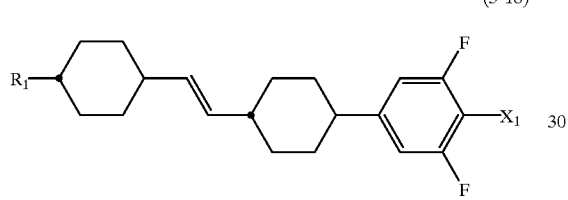
(3-19) 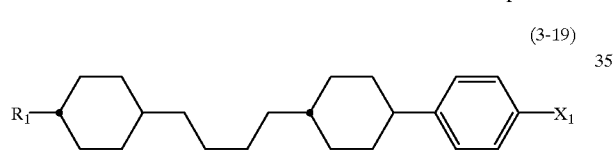
(3-20) 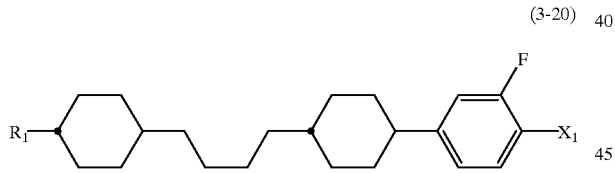
(3-21) 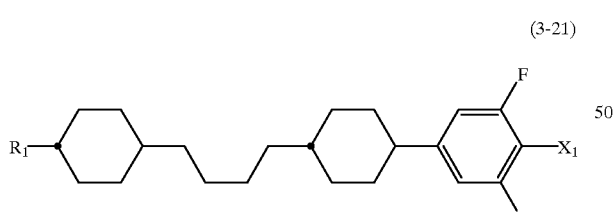
(3-22) 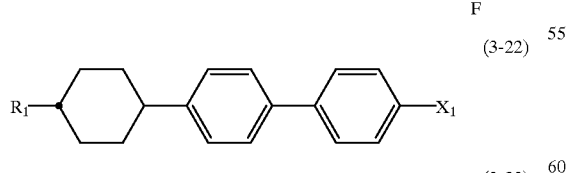
(3-23) 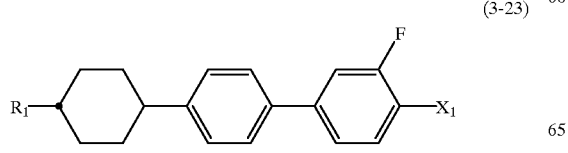
(3-24) 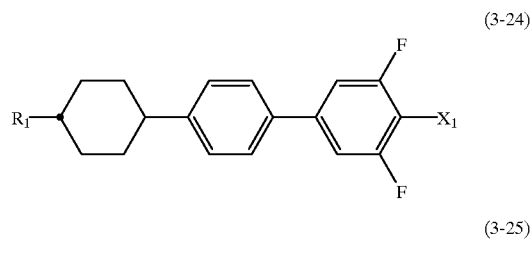
(3-25) 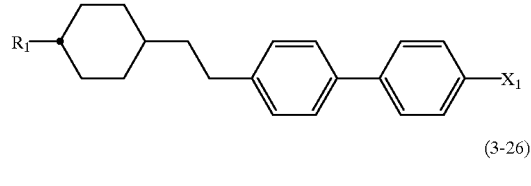
(3-26) 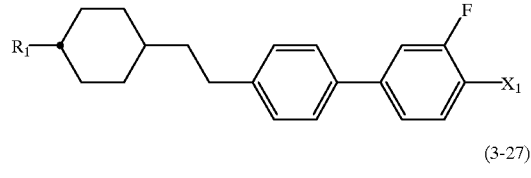
(3-27) 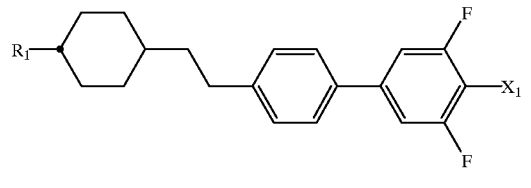
(3-28) 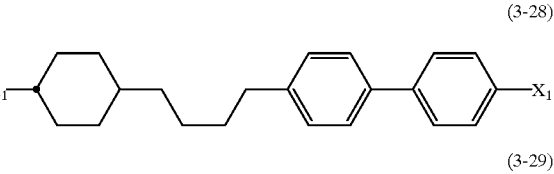
(3-29) 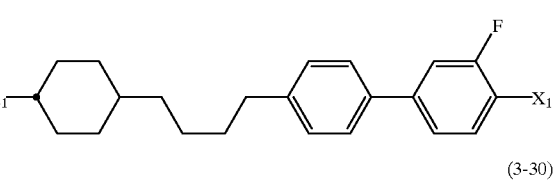
(3-30) 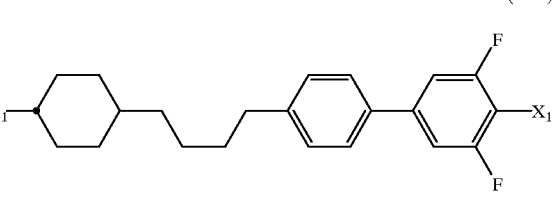
(3-31) 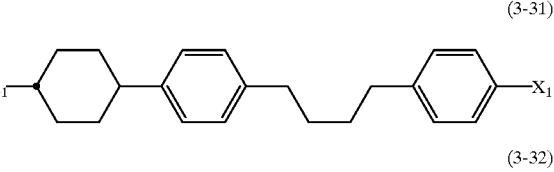
(3-32) 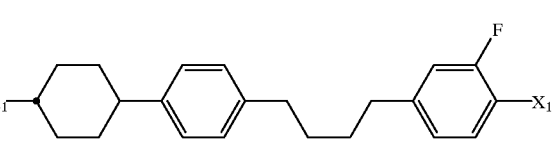

(3-33)
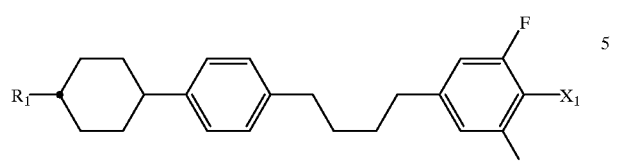
(3-34)
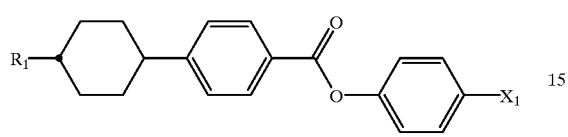
(3-35)
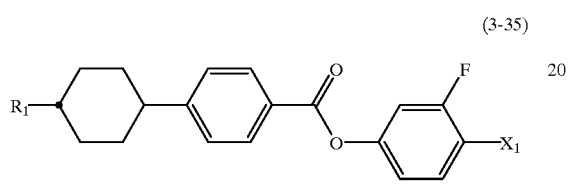
(3-36)
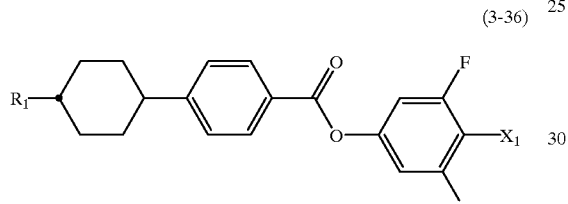
(3-37)
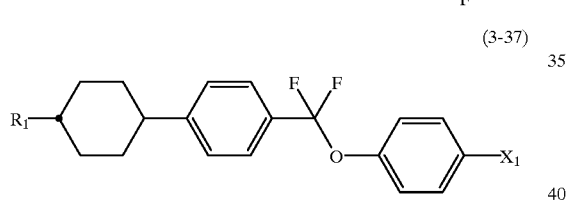
(3-38)
(3-39)
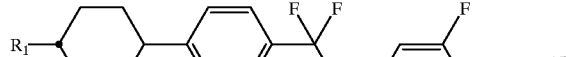
(3-40)
(3-41)
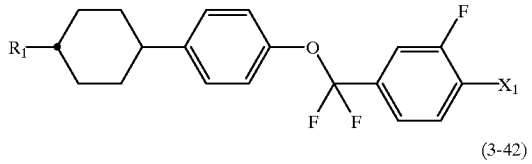
(3-42)
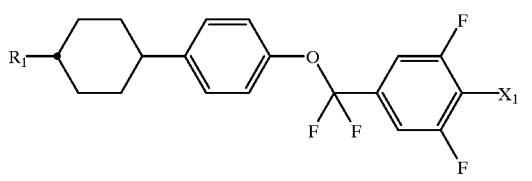
(3-43)
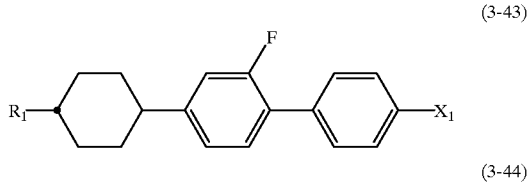
(3-44)
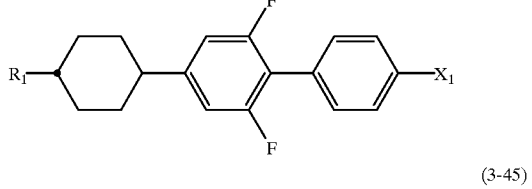
(3-45)
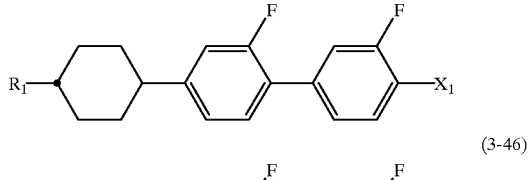
(3-46)
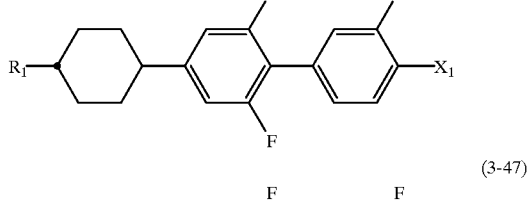
(3-47)
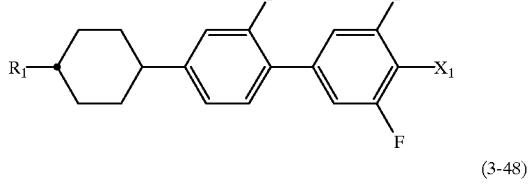
(3-48)
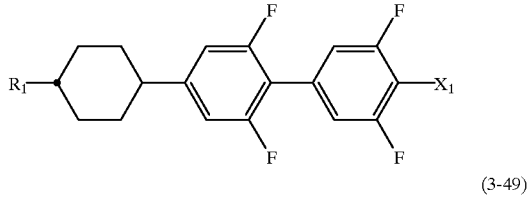
(3-49)
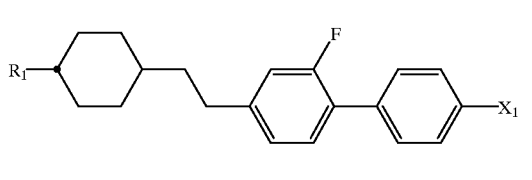

(3-50)
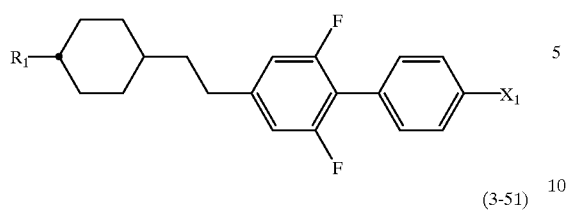
(3-51)
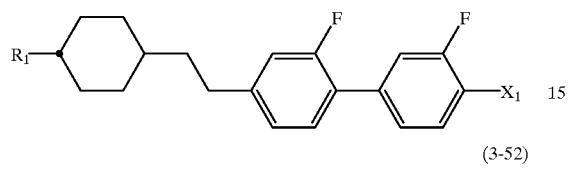
(3-52)
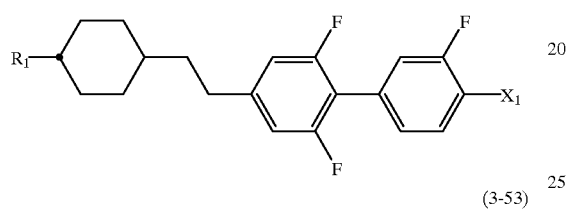
(3-53)
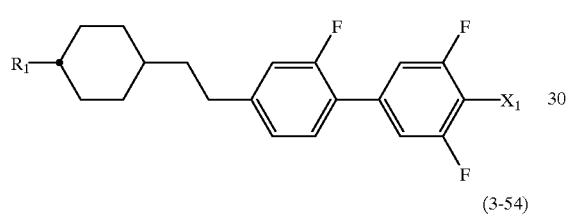
(3-54)
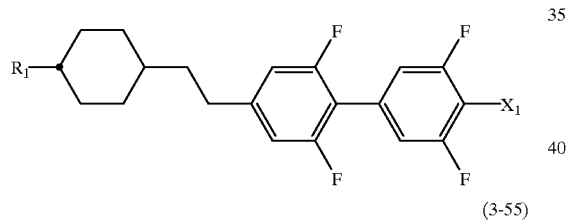
(3-55)
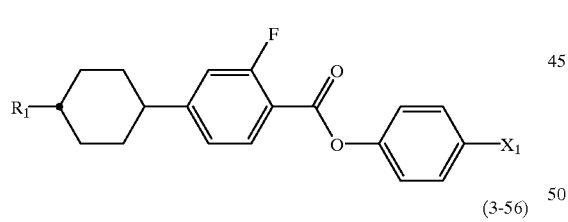
(3-56)
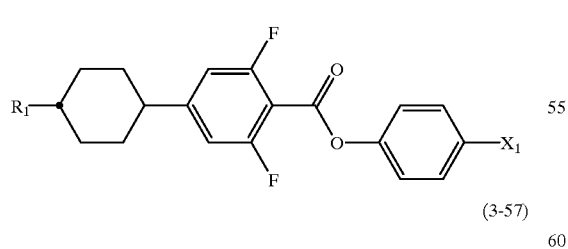
(3-57)
(3-58)
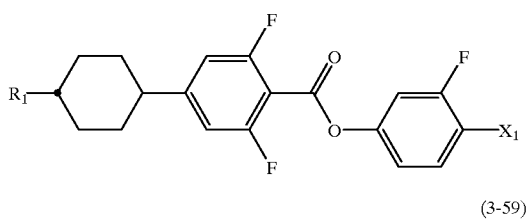
(3-59)
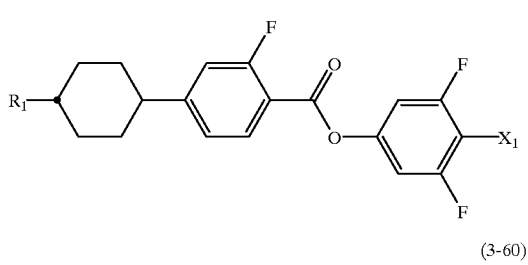
(3-60)
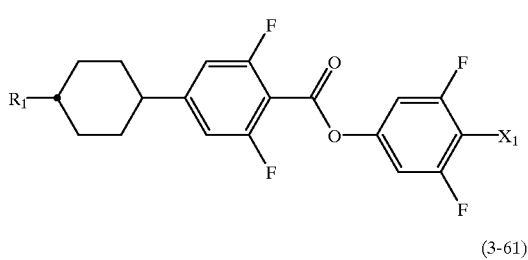
(3-61)
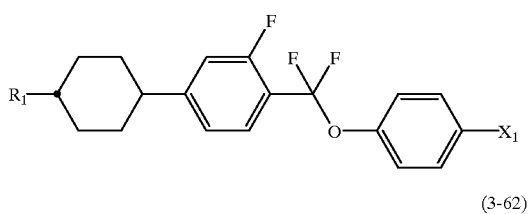
(3-62)
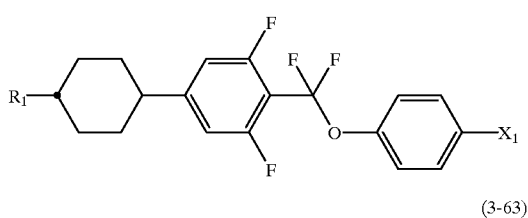
(3-63)
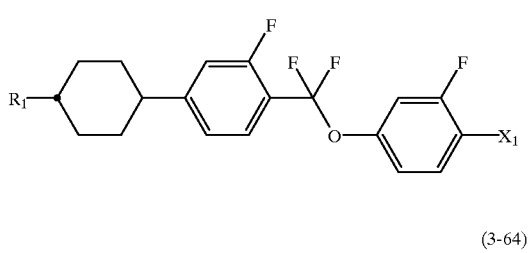
(3-64)
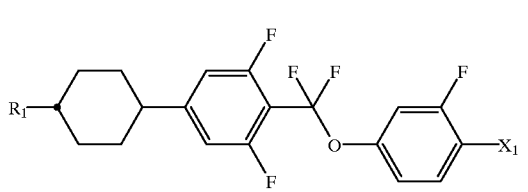

(3-65)
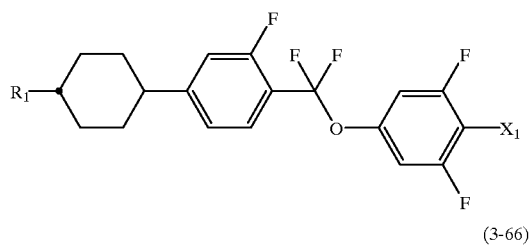
(3-66)
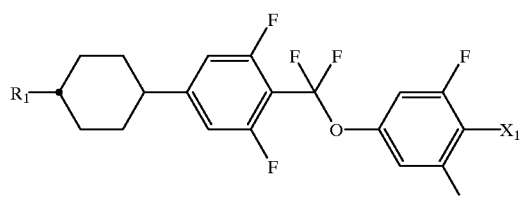
(3-67)
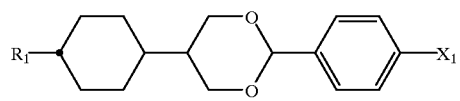
(3-68)
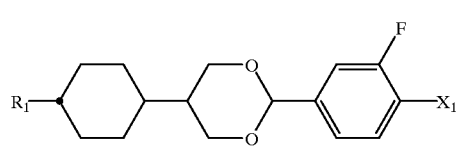
(3-69)
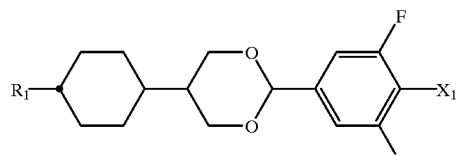
(4-1)
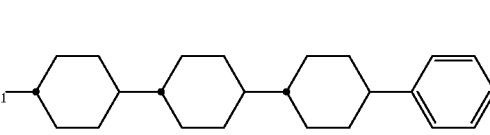
(4-2)
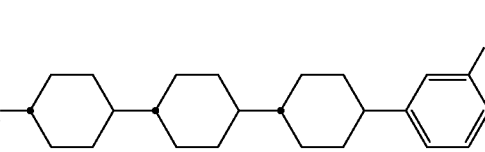
(4-3)
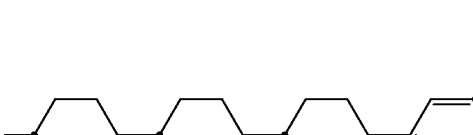
(4-4)
(4-5)
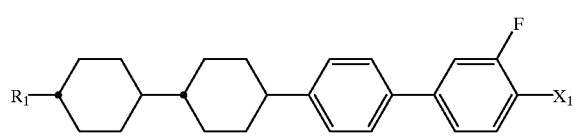
(4-6)
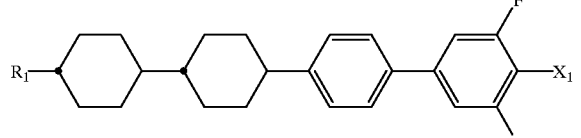
(4-7)
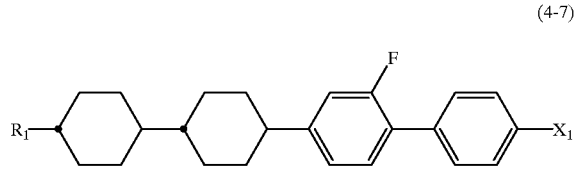
(4-8)
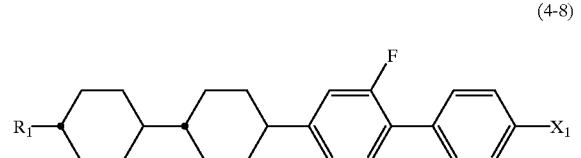
(4-9)
(4-10)
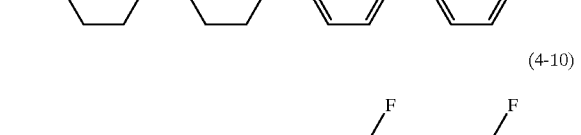
(4-11)
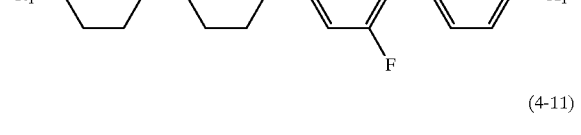
(4-12)
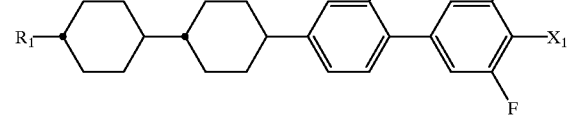

(4-13) 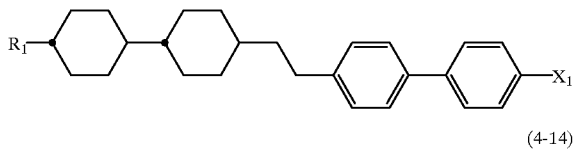

(4-14) 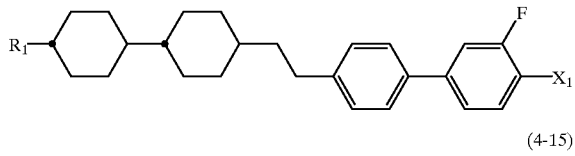

(4-15) 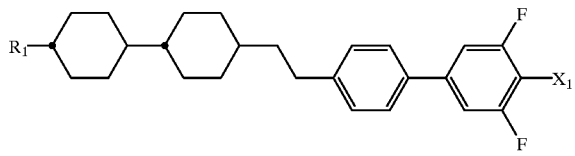

(4-16) 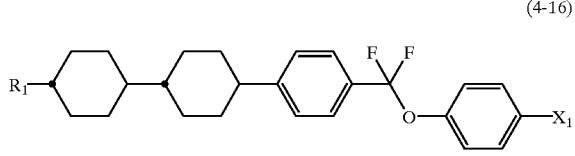

(4-17) 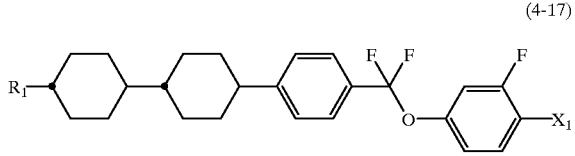

(4-18) 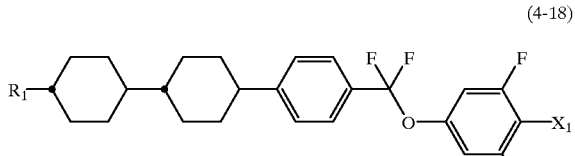

(4-19) 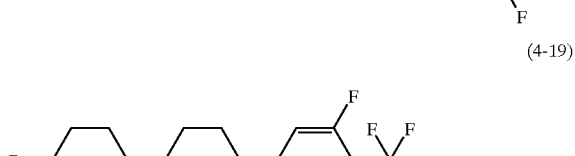

(4-20) 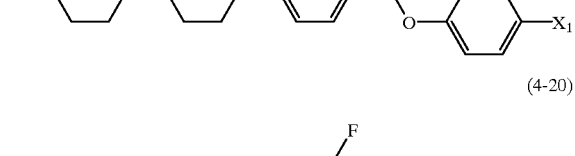

(4-21) 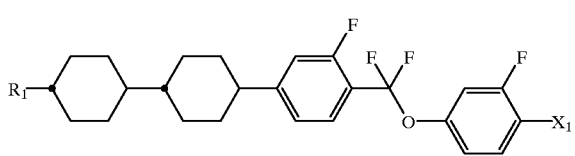

(4-22) 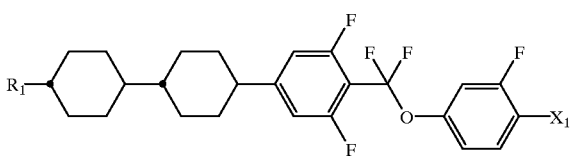

(4-23) 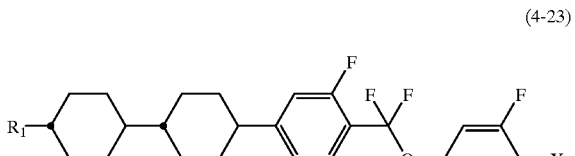

(4-24) 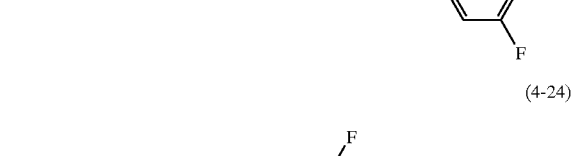

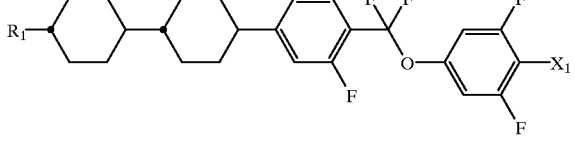

wherein $R_1$ and $X_1$ have the same meaning as described above.

Compounds expressed by one of the general formulas (2) to (4) have a positive dielectric anisotropy value, are remarkably excellent in thermal stability and chemical stability, and are indispensable when liquid crystal compositions for TFT are produced of which a high reliability such as a particularly high voltage holding ratio or large specific resistivity is required.

While the compound expressed by one of the general formulas (2) to (4) can be used in the range of 0.1 to 99.9% by weight based on the total amount of liquid crystal composition when liquid crystal compositions for TFT are produced, the amount is preferably 10 to 97% by weight and more desirably 40 to 95% by weight. Further, the compound expressed by one of the general formulas (7) to (9) may further be incorporated for the purpose of adjusting viscosity of liquid crystal compositions. Also, when liquid crystal compositions for STN display mode or TN display mode are produced, the compound expressed by one of the general formulas (2) to (4) can be used. In this case, the amount of the compound to be used is preferably less than 50% by weight.

As the compounds used in the liquid crystal compositions of the present invention and expressed by the general formula (5) or (6), the following compounds can preferably be mentioned:

(5-1) 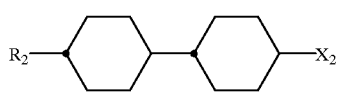
(5-2) 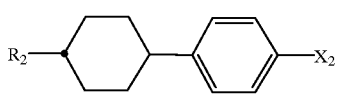
(5-3) 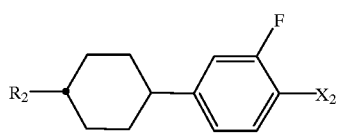
(5-4) 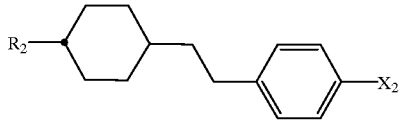
(5-5) 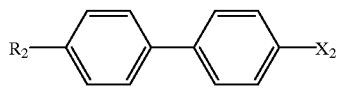
(5-6) 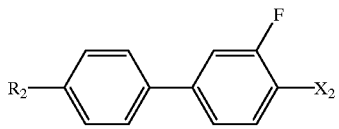
(5-7) 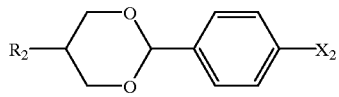
(5-8) 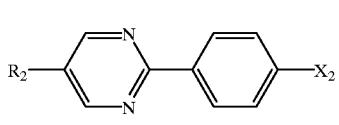
(5-9) 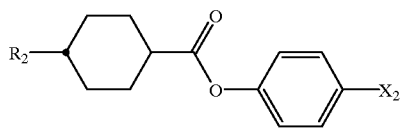
(5-10) 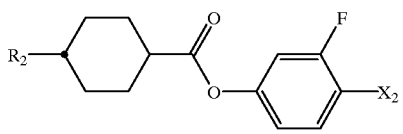
(5-11) 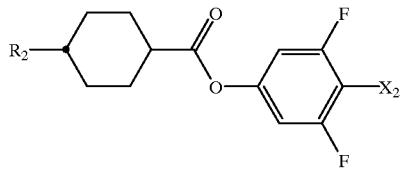
(5-12) 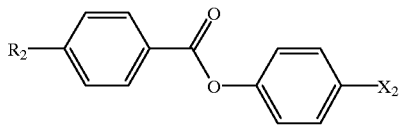
(5-13) 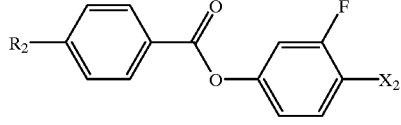
(5-14) 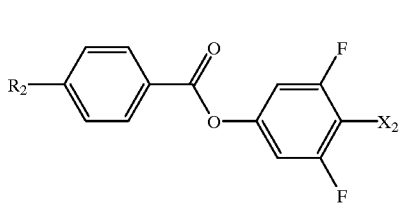
(5-15) 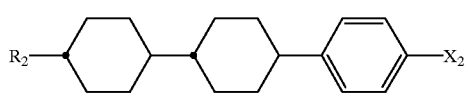
(5-16) 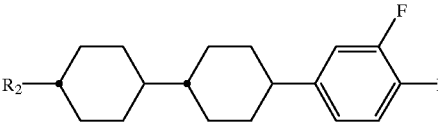
(5-17) 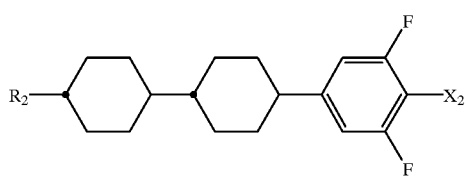
(5-18) 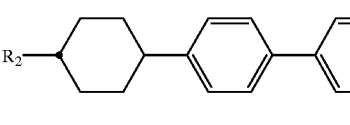
(5-19) 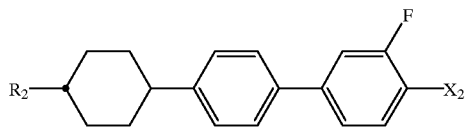
(5-20) 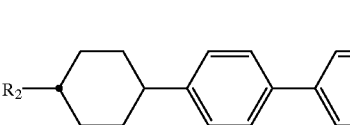

(5-21)
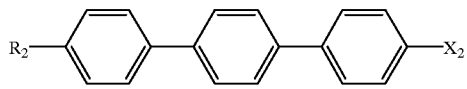
(5-22)
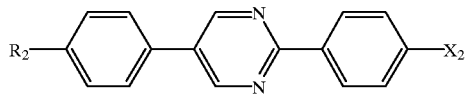
(5-23)
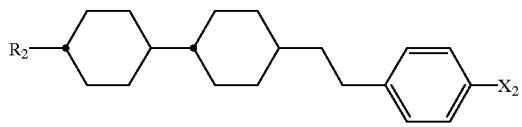
(5-24)
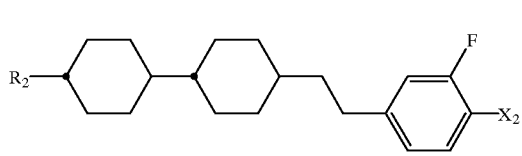
(5-25)
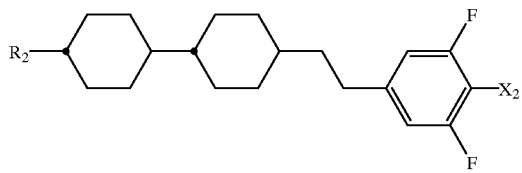
(5-26)
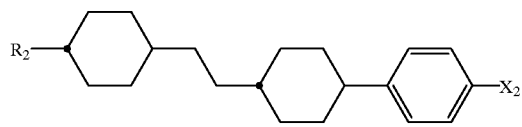
(5-27)
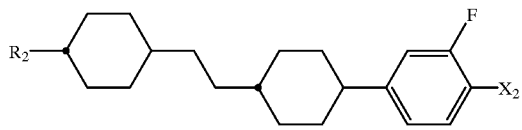
(5-28)
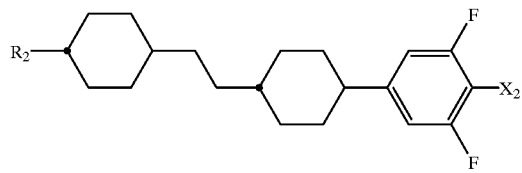
(5-29)
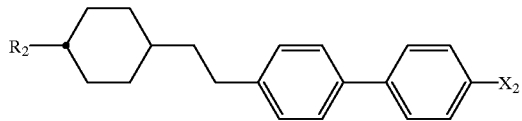
(5-30)
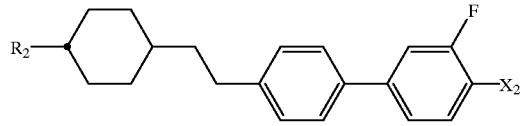
(5-31)
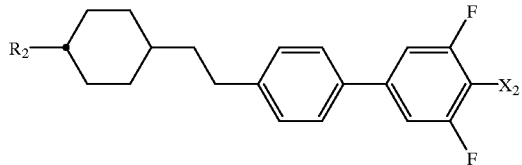
(5-32)
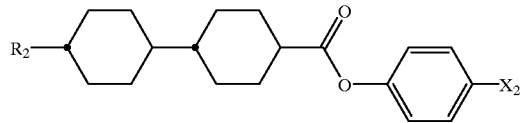
(5-33)
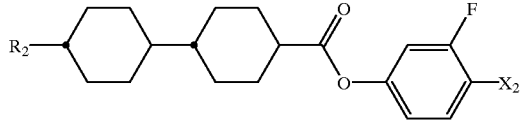
(5-34)
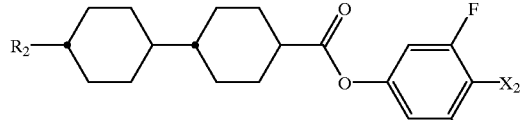
(5-35)
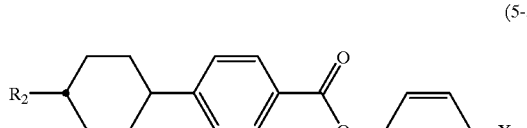
(5-36)
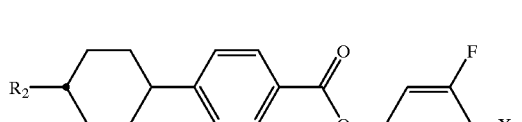

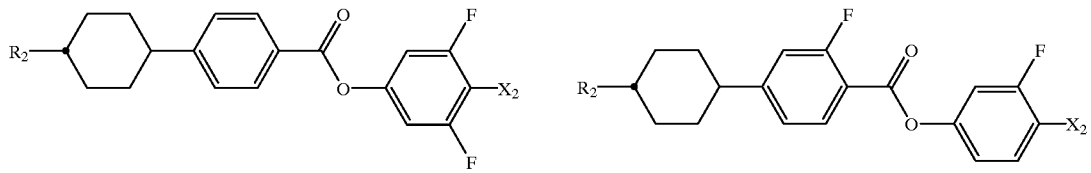
(5-37) (5-38)

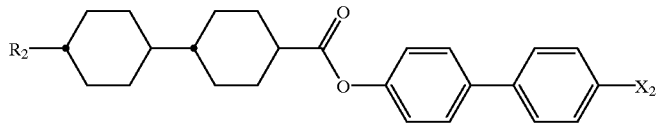
(5-39)

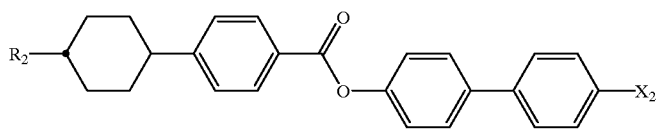
(5-40)

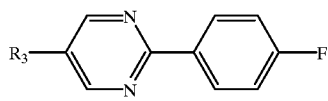
(6-1)

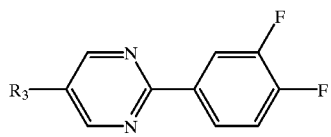
(6-2)

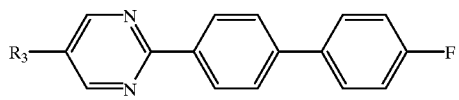
(6-3)

wherein $R_2$, $R_3$, and $X_2$ have the same meaning as described above.

Compounds expressed by the general formula (5) or (6) have a positive and high dielectric anisotropy value, and are used particularly for the purpose of lowering threshold voltage of liquid crystal compositions. They are also used for the purpose of adjusting optical anisotropy value, and widening nematic range such as raising clearing point. Further, they are used for the purpose of improving the steepness of V-T curve of liquid crystal compositions for STN or TN.

Compounds expressed by the general formula (5) or (6) are useful particularly when liquid crystal compositions for STN or TN are produced.

When the amount of the compound expressed by the general formula (5) or (6) to be used is increased, threshold voltage of liquid crystal compositions lowers and viscosity rises. Accordingly, it is advantageous to use the compound in a large amount so far as the viscosity of liquid crystal compositions satisfies required characteristics since the compositions become possible to be driven at a low voltage. While the compound expressed by the general formula (5) or (6) can be used in any amount in the range of 0.1 to 99.9% by weight when liquid crystal compositions for STN or TN are produced, and the range is preferably 10 to 97% by weight and more desirably 40 to 95% by weight.

As the compounds used in the liquid crystal compositions of the present invention and expressed by any one of the general formulas (7) to (9), the following compounds can preferably be mentioned:

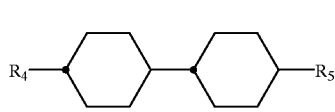
(7-1)

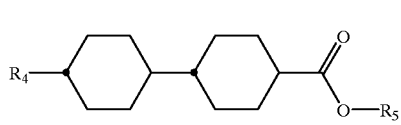
(7-2)

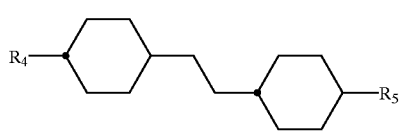
(7-3)

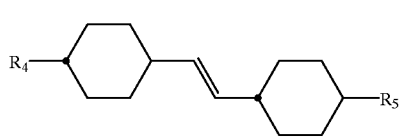
(7-4)

-continued
(7-5)
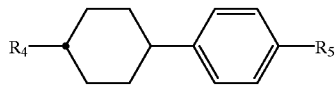
(7-6)
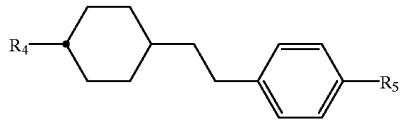
(7-7)
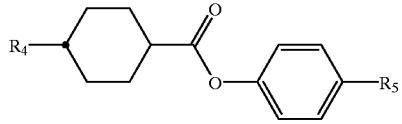
(7-8)
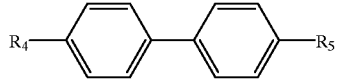
(7-9)
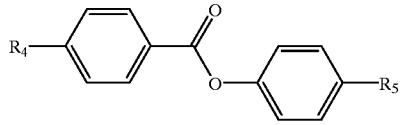
(7-10)
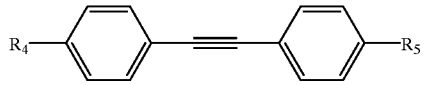
(7-11)
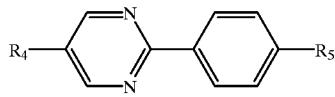
(8-1)
(8-2)
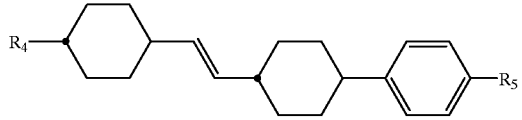
(8-3)
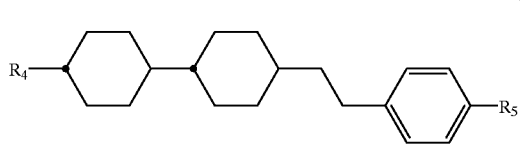
(8-4)
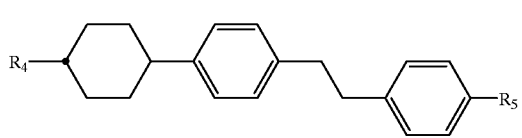
(8-5)
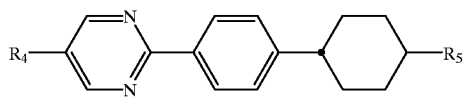
(8-6)
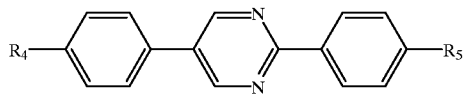
(8-7)
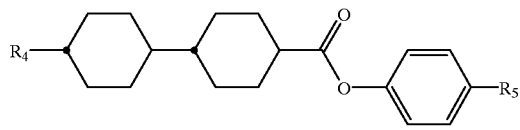
(8-8)
(8-9)
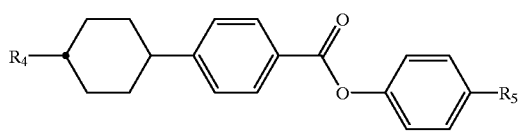
(8-10)
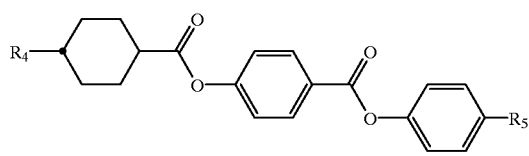
(8-11)
(8-12)

-continued
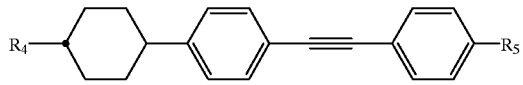 (8-13)
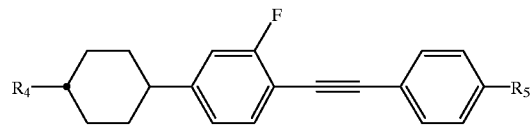 (8-14)
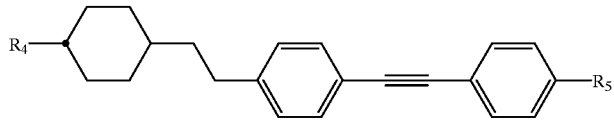 (8-15)
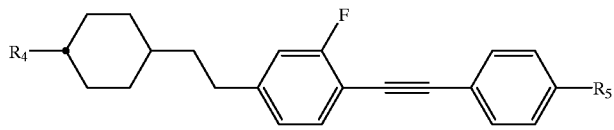 (8-16)
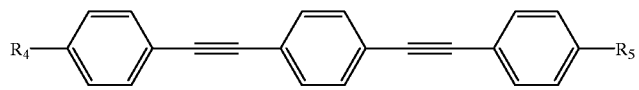 (8-17)
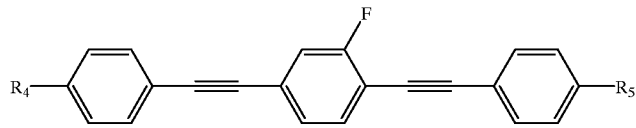 (8-18)
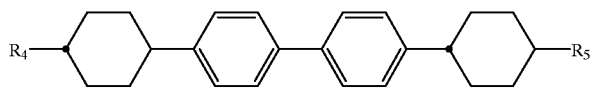 (9-1)
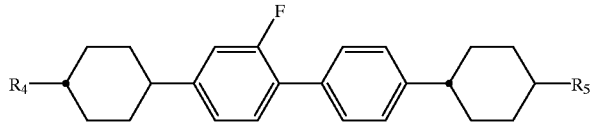 (9-2)
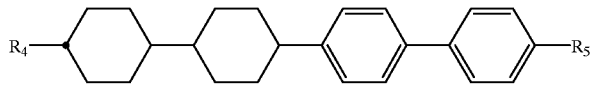 (9-3)
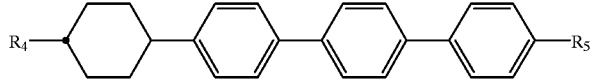 (9-4)
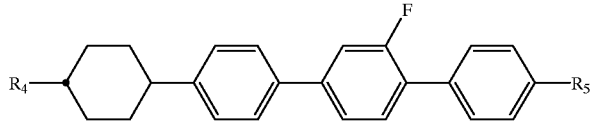 (9-5)
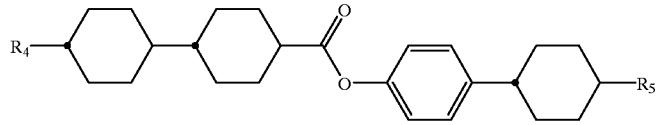 (9-6)

wherein $R_4$ and $R_5$ have the same meaning as described above.

Compounds expressed by one of the general formulas (7) to (9) are small in its absolute value of dielectric anisotropy and are close to neutral. Compounds expressed by the general formula (7) are used principally for the purpose of adjusting viscosity or adjusting optical anisotropy value. Compounds expressed by the general formula (8) or (9) are used for the purpose of widening nematic range such as raising clearing point, or for the purpose of adjusting optical anisotropy value.

When the amount of the compound expressed by one of the general formulas (7) to (9) is increased, threshold voltage of liquid crystal compositions rises and viscosity reduces. Accordingly, it is desirable to use the compound in a large amount so far as liquid crystal compositions satisfy the required value of threshold voltage. The amount of the compound expressed by one of the general formulas (7) to (9) to be used is preferably less than 40% by weight when liquid crystal compositions for TFT are produced and the amount is more desirably less than 35% by weight. When liquid crystal compositions for STN or TN are produced, the amount is preferably less than 70% by weight and more desirably less than 50% by weight.

As preferable examples of the compounds used in the liquid crystal compositions of the present invention and expressed by one of the general formulas (10) to (12), the following compounds can be mentioned:

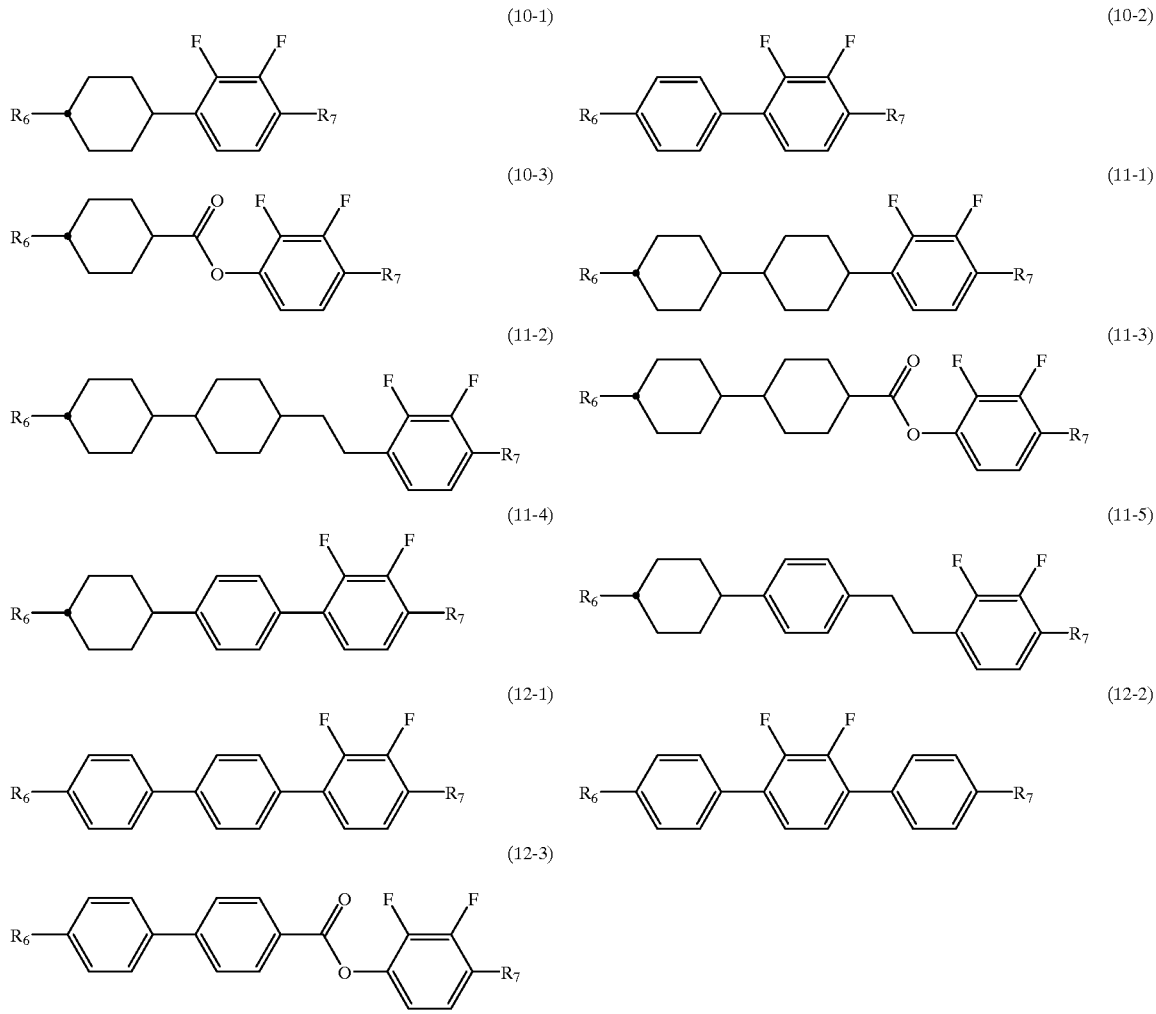

wherein $R_6$ and $R_7$ have the same meaning as described above.

Compounds expressed by one of the general formulas (10) to (12) have a negative dielectric anisotropy value. Since the compounds expressed by the general formula (10) are two rings compounds, they are used principally for the purpose of adjusting threshold voltage, adjusting viscosity, or adjusting optical anisotropy value. Compounds expressed by the general formula (11) are used for the purpose of widening nematic range such as raising clearing point, or for the purpose of adjusting optical anisotropy value. Compounds expressed by the general formula (12) are used for the purpose of lowering threshold voltage and for the purpose of increasing optical anisotropy value in addition to the purpose of widening nematic range.

Compounds expressed by one of the general formulas (10) to (12) are principally used for liquid crystal compositions having a negative anisotropy value, and when their amount to be used is increased, threshold voltage of the compositions lowers and viscosity increases. Accordingly, it is desirable to use them in a small amount so far as the compositions satisfy a required value of threshold voltage. However, since absolute value of dielectric anisotropy of these compounds is lower than 5, when the amount becomes less than 40% by weight, the liquid crystal compositions sometimes become impossible to be driven at a low voltage. The amount of the compounds expressed by one of the general formulas (10) to (12) to be used is preferably more than 40% by weight when liquid crystal compositions for TFT having a negative dielectric anisotropy value are produced, and the amount is more desirably 50 to 90% by weight. Further, the compounds expressed by one of the general formulas (10) to (12) are sometimes mixed to liquid crystal compositions having a positive dielectric anisotropy value for the purpose of controlling the elastic constant and regulating the V-T curve of the compositions. In this case, the amount of the compounds expressed by one of the general formulas (10) to (12) to be used is preferably less than 30% by weight.

With the exception of such specific cases as liquid crystal compositions for OCB (optically Compensated Birefringence) and the likes, an optically active compound is usually added to the liquid crystal compositions of the present invention for the purpose of inducing helical structure of liquid crystal composition to adjust required twist angle and to prevent reverse twist. As the optically active compound, any known optically active compounds ordinarily used for such purposes can be used, but examples of more preferable optically active compounds can be mentioned as follows:

(Symbol: C15)
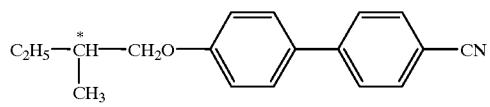

(Symbol: CB15)
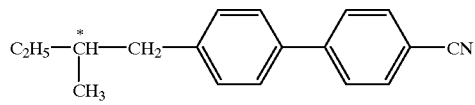

(Symbol: CM21)
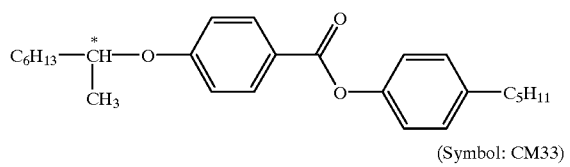

(Symbol: CM33)
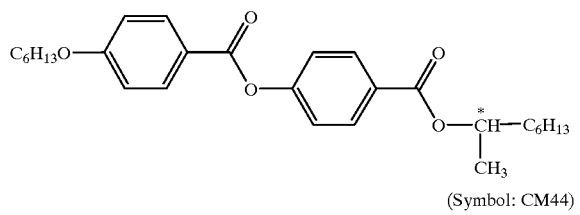

(Symbol: CM44)
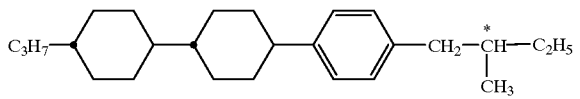

(Symbol: CM45)
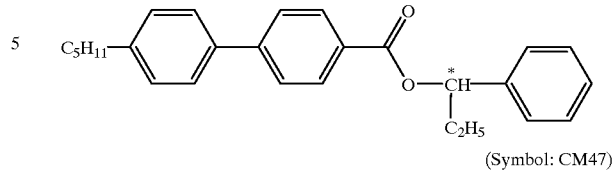

(Symbol: CM47)
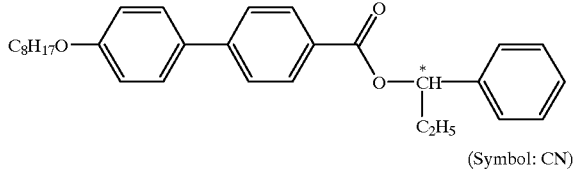

(Symbol: CN)
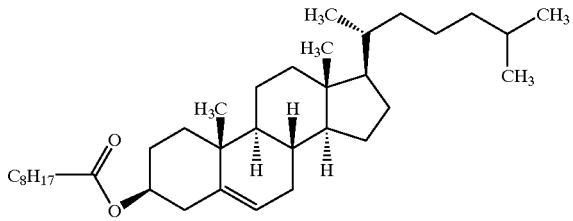

Liquid crystal compositions of the present invention are usually adjusted in their pitch of twist by adding these optically active compounds thereto. The twist pitch is preferably adjusted in the range of 40 to 200 $\mu$m in the case of liquid crystal compositions for TFT or TN, and preferably adjusted in the range of 6 to 20 $\mu$m in the case of liquid crystal compositions for STN. In the case for bistable TN mode, it is preferable to adjust the pitch in the range of 1.5 to 4 $\mu$m. Further, two or more kind of optically active compounds may be added for the purpose of adjusting the dependency of pitch on temperature.

Liquid crystal compositions of the present invention can be produced by conventional methods. Generally, a method in which various components are dissolved in one another at a high temperature has been adopted.

Further, the liquid crystal compositions of the present invention can be used as ones for guest-host (GH) mode by adding a dichroic dye such as merocyanine type, styryl type, azo type, azomethine type, azoxy type, quinophthalone type, anthraquinone type, and tetrazine type thereto. Alternatively, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for electrically controlled birefringence (ECB) mode or dynamic scattering (DS) mode.

As examples of liquid crystal compositions comprising the compound of the present invention, the followings can be mentioned. The compounds in Composition Examples, and Examples described below are designated by symbolizing them according to the definition shown below, and the compound No. in Composition Examples is given in the same rule as that shown in Examples.

| Ring structure | Symbol | Ring structure | Symbol |
|---|---|---|---|
|  | B | 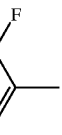 | B(3,5F) |
| 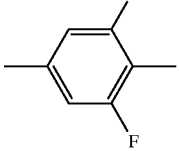 | B(2F) | 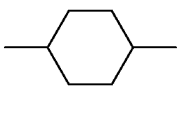 | B(3F, 5Cl) |
| 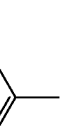 | B(3F) | 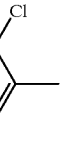 | H |
| 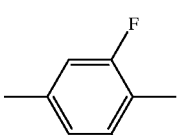 | B(3Cl) | 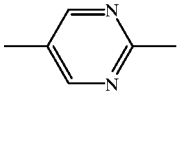 | Py |
| 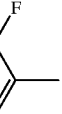 | B(2,3F) | 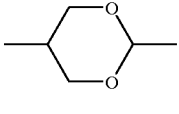 | D(3,5) |
| 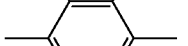 | B(2,3Cl) | 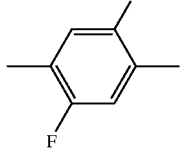 | Ch |
| 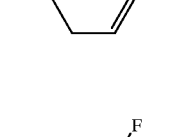 | B(2,5F) |  | B(3,6F) |

| Right side terminal group Rd | Symbol |
|---|---|
| —F | —F |
| —Cl | —CL |
| —CN | —C |
| —CF$_3$ | —CF$_3$ |
| —OCF$_3$ | —OCF3 |
| —OCF$_2$H | —OCF$_2$H |
| —OCF$_2$CF$_2$H | —OCF$_2$CF$_2$H |
| —OCF$_2$CFHCF$_3$ | —OCF$_2$CFHCF$_3$ |
| —C$_w$H$_{2w+1}$ | —w |
| —OC$_2$H$_{2w+1}$ | —Ow |
| —C$_w$H$_{2w}$CH=CH$_2$ | —wV |
| —C$_w$H$_{2w}$CH=CHC$_x$H$_{2x+1}$ | —wVx |
| —COOCH$_3$ | —EMe |
| —C$_w$H$_{2w}$CH=CHC$_x$H$_{2x}$F | —wVxF |
| —CH=CF$_2$ | —VFF |
| —C$_w$H$_{2w}$CH=CF$_2$ | —wVFF |
| —C≡C—CN | —TC |

| Ring structure | Symbol | Ring structure | Symbol |
|---|---|---|---|
| 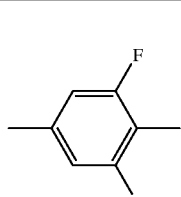 | B | 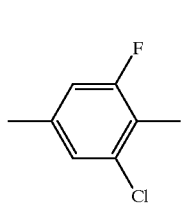 | B(3,5F) |
| 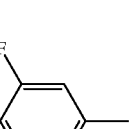 | B(2F) | 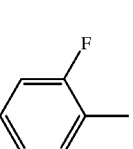 | B(3F,5Cl) |
| 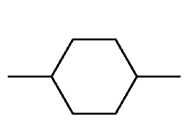 | B(3F) | 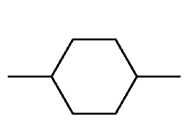 | H |

-continued

| Right side terminal group Rd | Symbol |
|---|---|
| —F | —F |
| —Cl | —CL |
| —CN | —C |
| —CF$_3$ | —CF$_3$ |
| —OCF$_3$ | —OCF3 |
| —OCF$_2$H | —OCF$_2$H |
| —OCF$_2$CF$_2$H | —OCF$_2$CF$_2$H |
| —OCF$_2$CFHCF$_3$ | —OCF$_2$CFHCF$_3$ |
| —C$_w$H$_{2w+1}$ | —w |
| —OC$_w$H$_{2w+1}$ | —Ow |
| —C$_w$H$_{2w}$CH=CH$_2$ | —wV |
| —C$_w$H$_{2w}$CH=CHC$_x$H$_{2x+1}$ | —wVx |
| —COOCH$_3$ | —EMe |
| —C$_w$H$_{2w}$CH=CHC$_x$H$_{2x}$F | —wVxF |
| —CH=CF$_2$ | —VFF |
| —C$_w$H$_{2w}$CH=CF$_2$ | —wVFF |
| —C≡C—CN | —TC |

When hydrogen atom of trans-1,4-cyclohexylene in the following partial structure was replaced by deuterium (heavy hydrogen) at positions $Q_1$, $Q_2$, and $Q_3$, it is designated by symbol H[1D 2D, 3D], and when the positions $Q_5$, $Q_6$, and $Q_7$ were replaced by deuterium, it is designated by symbol H[5D, 6D, 7D]. In other words, the positions where deuterium substituted are indicated by the numeral in the bracket [ ].

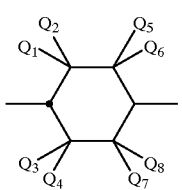

In the Composition Examples and Examples, "%" means % by weight and "part" means the amount (part by weight) of an optically active compound to be added to 100 parts by weight of a liquid crystal composition unless otherwise specified. When cis·trans isomers exist in particular compounds, they are trans form.

COMPOSITION EXAMPLE 1

| | |
|---|---|
| 3-B(3F)B(3,5F)B(3F)B(3F)-CL (Compound No. 49) | 1.0% |
| 2-BBB(3,5F)B(3F)-OCF$_3$ (Compound No. 10) | 1.0% |
| 1V2-BEB(3,5F)-C | 5.0% |
| 3-HB-C | 25.0% |
| 1-BTB-3 | 5.0% |
| 2-BTB-1 | 10.0% |
| 3-HH-4 | 11.0% |
| 3-HHB-1 | 9.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(3F)TB-2 | 6.0% |
| 3-HB(3F)TB-3 | 6.0% |
| CM33 | 0.8 part |

COMPOSITION EXAMPLE 2

| | |
|---|---|
| 2-BBB(3,5F)B(3F)-OCF$_3$ (Compound No. 10) | 2.0% |
| V2-HB-C | 12.0% |
| 1V2-HB-C | 12.0% |
| 3-HB-C | 15.0% |
| 3-H[1D,2D,3D]B-C | 9.0% |
| 3-HB(3F)-C | 5.0% |
| 2-BTB-1 | 2.0% |
| 3-HH-4 | 8.0% |
| 3-HH-VFF | 6.0% |
| 2-H[1D,2D,3D]HB-C | 3.0% |
| 3-HHB-C | 6.0% |
| 3-HB(3F)TB-2 | 8.0% |
| 3-H2BTB-2 | 5.0% |
| 3-H2BTB-3 | 5.0% |
| 3-H2BTB-4 | 2.0% |

COMPOSITION EXAMPLE 3

| | |
|---|---|
| 3-B2B(3F)B(3,5F)B(3F)-F (Compound No. 1) | 4.0% |
| 2O1-BEB(3F)-C | 5.0% |
| 3O1-BEB(3F)-C | 15.0% |
| 4O1-BEB(3F)-C | 13.0% |
| 5O1-BEB(3F)-C | 13.0% |
| 2-HHB(3F)-C | 15.0% |
| 3-HHB(3F)-C | 15.0% |
| 3-HB(3F)TB-2 | 4.0% |
| 3-HB(3F)TB-3 | 4.0% |
| 3-HHB-1 | 8.0% |
| 3-HHB-O1 | 4.0% |

COMPOSITION EXAMPLE 4

| | |
|---|---|
| 3-B(3F)B(3,5F)B(3F)B(3F)-CL (Compound No. 49) | 1.0% |
| 2-BBB(3,5F)B(3F)-OCF$_3$ (Compound No. 10) | 2.0% |
| 5-PyB-F | 4.0% |
| 3-PyB(3F)-F | 4.0% |
| 2-BB-C | 5.0% |
| 4-BB-C | 4.0% |
| 5-BB-C | 5.0% |
| 2-PyB-2 | 2.0% |
| 3-PyB-2 | 2.0% |
| 4-PyB-2 | 2.0% |
| 6-PyB-O5 | 3.0% |
| 6-PyB-O6 | 3.0% |
| 6-PyB-O7 | 3.0% |
| 6-PyB-O8 | 3.0% |
| 3-PyBB-F | 6.0% |
| 4-PyBB-F | 6.0% |
| 5-PyBB-F | 6.0% |
| 3-HHB-1 | 6.0% |
| 3-HHB-3 | 5.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

COMPOSITION EXAMPLE 5

| | |
|---|---|
| 2-BBB(3,5F)B(3F)-OCF$_3$ (Compound No. 10) | 2.0% |
| 3-B2B(3F)B(3,5F)B(3F)-F (Compound No. 1) | 2.0% |
| 3-D(3,5)B-C | 10.0% |
| 4-D(3,5)B-C | 10.0% |
| 2-BEB-C | 12.0% |
| 3-BEB-C | 4.0% |
| 3-PyB(3F)-F | 6.0% |
| 3-HEB-O4 | 8.0% |
| 4-HEB-O2 | 6.0% |
| 5-HEB-O1 | 6.0% |
| 3-HEB-O2 | 5.0% |
| 5-HEB-O2 | 4.0% |
| 5-HEB-5 | 5.0% |
| 4-HEB-5 | 5.0% |
| 1O-BEB-2 | 4.0% |
| 3-HHB-1 | 4.0% |
| 3-HHEBB-C | 3.0% |
| 3-HBEBB-C | 2.0% |
| 5-HBEBB-C | 2.0% |

COMPOSITION EXAMPLE 6

| | |
|---|---|
| 3-B(3F)B(3,5F)B(3F)B(3F)-CL (Compound No. 49) | 1.0% |
| 3-B2B(3F)B(3,5F)B(3F)-F (Compound No. 1) | 5.0% |
| 3-HB-C | 18.0% |
| 7-HB-C | 3.0% |
| 1O1-HB-C | 10.0% |
| 3-HB(3F)-C | 10.0% |
| 2-PyB-2 | 2.0% |
| 3-PyB-2 | 2.0% |
| 4-PyB-2 | 2.0% |
| 1O1-HH-3 | 7.0% |
| 2-BTB-O1 | 7.0% |
| 3-HHB-1 | 7.0% |
| 3-HHB-F | 4.0% |
| 3-HHB-O1 | 4.0% |
| 3-HHB-3 | 5.0% |
| 3-H2BTB-3 | 3.0% |
| 2-PyBH-3 | 4.0% |
| 3-PyBH-3 | 3.0% |
| 3-PyBB-2 | 3.0% |

COMPOSITION EXAMPLE 7

| | |
|---|---|
| 3-B(3F)B(3,5F)B(3F)B(3F)-CL (Compound No. 49) | 1.0% |
| 2-BBB(3,5F)B(3F)-OCF$_3$ (Compound No. 10) | 2.0% |
| 3-B2B(3F)B(3,5F)B(3F)-F (Compound No. 1) | 3.0% |
| 2O1-BEB(3F)-C | 5.0% |
| 3O1-BEB(3F)-C | 12.0% |
| 5O1-BEB(3F)-C | 4.0% |
| 1V2-BEB(3,5F)-C | 10.0% |
| 3-HH-EMe | 10.0% |
| 3-HB-O2 | 18.0% |
| 7-HEB-F | 2.0% |
| 3-HHEB-F | 2.0% |
| 5-HHEB-F | 2.0% |
| 3-HBEB-F | 4.0% |
| 2O1-HBEB(3F)-C | 2.0% |
| 3-HB(3F)EB(3F)-C | 2.0% |
| 3-HBEB(3,5F)-C | 2.0% |
| 3-HHB-F | 4.0% |
| 3-HHB-O1 | 4.0% |
| 3-HHB-3 | 7.0% |
| 3-HEBEB-F | 2.0% |
| 3-HEBEB-1 | 2.0% |

COMPOSITION EXAMPLE 8

| | |
|---|---|
| 4O-B(2,3F)BB(2,3F)2B-3 (Compound No. 147) | 3.0% |
| 5-BEB(3F)-C | 5.0% |
| V-HB-C | 11.0% |
| 5-PyB-C | 6.0% |
| 4-BB-3 | 11.0% |
| 3-HH-2V | 10.0% |
| 5-HH-V | 11.0% |
| V-HHB-1 | 7.0% |
| V2-HHB-1 | 12.0% |
| 3-HHB-1 | 9.0% |
| 1V2-HBB-2 | 10.0% |
| 3-HHEBH-3 | 5.0% |

COMPOSITION EXAMPLE 9

| | |
|---|---|
| 3-BB(3,5F)CH$_2$OBB(3,5F)-CF$_3$ (Compound No. 179) | 2.0% |
| 2O1-BEB(3F)-C | 5.0% |
| 3O1-BEB(3F)-C | 12.0% |
| 5O1-BEB(3F)-C | 4.0% |
| 1V2-BEB(3,5F)-C | 16.0% |
| 3-HB-O2 | 10.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB(3F)TB-2 | 3.0% |

COMPOSITION EXAMPLE 10

| | |
|---|---|
| 3-B(3F)B(3,5F)B(3F)B(3F)-CL (Compound No. 49) | 1.0% |
| 2-BBB(3,5F)B(3F)-OCF$_3$ (Compound No. 10) | 1.0% |
| 3-B2B(3F)B(3,5F)B(3F)-F (Compound No. 1) | 2.0% |
| 2-BEB-C | 12.0% |
| 3-BEB-C | 4.0% |
| 4-BEB-C | 6.0% |
| 3-HB-C | 28.0% |
| 3-HEB-O4 | 12.0% |
| 4-HEB-O2 | 8.0% |
| 5-HEB-O1 | 8.0% |
| 3-HEB-O2 | 6.0% |
| 5-HEB-O2 | 5.0% |
| 3-HHB-1 | 3.0% |
| 3-HHB-O1 | 4.0% |

COMPOSITION EXAMPLE 11

| | |
|---|---|
| 3-B2B(3F)B(3,5F)B(3F)-F (Compound No. 1) | 5.0% |
| 4O-B(2,3F)BB(2,3F)2B-3 (Compound No. 147) | 3.0% |
| 3-BB(3,5F)CH$_2$OBB(3,5F)-CF$_3$ (Compound No. 179) | 2.0% |
| 2-BEB-C | 10.0% |
| 5-BB-C | 12.0% |
| 7-BB-C | 7.0% |
| 1-BTB-3 | 7.0% |
| 2-BTB-1 | 10.0% |
| 1O-BEB-2 | 10.0% |
| 1O-BEB-5 | 12.0% |
| 2-HHB-1 | 4.0% |
| 3-HHB-F | 4.0% |
| 3-HHB-1 | 7.0% |
| 3-HHB-O1 | 4.0% |
| 3-HHB-3 | 3.0% |

COMPOSITION EXAMPLE 12

| | |
|---|---|
| 4O-B(2,3F)BB(2,3F)2B-3 (Compound No. 147) | 3.0% |
| 3-BB(3,5F)CH$_2$OBB(3,5F)-CF$_3$ (Compound No. 179) | 2.0% |
| 1V2-BEB(3,5F)-C | 8.0% |
| 3-HB-C | 10.0% |
| V2V-HB-C | 14.0% |
| V2V-HH-3 | 19.0% |
| 3-HB-O2 | 4.0% |
| 3-HHB-1 | 10.0% |
| 3-HHB-3 | 10.0% |
| 3-HB(3F)TB-2 | 4.0% |
| 3-HB(3F)TB-3 | 4.0% |
| 3-H2BTB-2 | 4.0% |
| 3-H2BTB-3 | 4.0% |
| 3-H2BTB-4 | 4.0% |

COMPOSITION EXAMPLE 13

| | |
|---|---|
| 2-BBB(3,5F)B(3F)-OCF$_3$ (Compound No. 10) | 2.0% |
| 3-B2B(3F)B(3,5F)B(3F)-F (Compound No. 1) | 2.0% |
| 5-BTB(3F)TB-3 | 10.0% |
| V2-HB-TC | 10.0% |
| 3-HB-TC | 10.0% |
| 3-HB-C | 10.0% |
| 5-HB-C | 7.0% |
| 5-BB-C | 3.0% |
| 2-BTB-1 | 10.0% |
| 2-BTB-O1 | 5.0% |
| 3-HH-4 | 5.0% |
| 3-HHB-1 | 6.0% |
| 3-HHB-3 | 11.0% |
| 3-H2BTB-2 | 3.0% |
| 3-H2BTB-3 | 3.0% |
| 3-HB(3F)TB-2 | 3.0% |

COMPOSITION EXAMPLE 14

| | |
|---|---|
| 3-B(3F)B(3,5F)B(3F)B(3F)-CL (Compound No. 49) | 1.0% |
| 3-B2B(3F)B(3,5F)B(3F)-F (Compound No. 1) | 2.0% |
| 1V2-BEB(3,5F)-C | 6.0% |
| 3-HB-C | 18.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 2.0% |
| 3-H2BTB-3 | 4.0% |
| 3-H2BTB-4 | 4.0% |
| 3-HHB-1 | 4.0% |

COMPOSITION EXAMPLE 15

| | |
|---|---|
| 3-B(3F)B(3,5F)B(3F)B(3F)-CL (Compound No. 49) | 1.0% |
| 2-BBB(3,5F)B(3F)-OCF$_3$ (Compound No. 10) | 2.0% |

-continued

| | |
|---|---|
| 3-B2B(3F)B(3,5F)B(3F)-F (Compound No. 1) | 3.0% |
| 2-HB-C | 5.0% |
| 3-HB-C | 12.0% |
| 3-HB-O2 | 15.0% |
| 2-BTB-1 | 3.0% |
| 3-HHB-1 | 8.0% |
| 3-HHB-F | 4.0% |
| 3-HHB-O1 | 5.0% |
| 3-HHB-3 | 8.0% |
| 3-HHEB-F | 4.0% |
| 5-HHEB-F | 4.0% |
| 2-HHB(3F)-F | 7.0% |
| 3-HHB(3F)-F | 7.0% |
| 5-HHB(3F)-F | 7.0% |
| 3-HHB(3,5F)-F | 5.0% |

COMPOSITION EXAMPLE 16

| | |
|---|---|
| 3-B(3F)B(3,5F)B(3F)B(3F)—CL (Compound No. 49) | 1.0% |
| 2-BBB(3,5F)B(3F)—OCF$_3$ (Compound No. 10) | 1.0% |
| 3-B2B(3F)B(3,5F)B(3F)—F (Compound No. 1) | 10.0% |
| 4O—B(2,3F)BB(2,3F)2B-3 (Compound No. 147) | 2.0% |
| 3-BB(3,5F)CH$_2$OBB(3,5F)—CF$_3$ (Compound No. 179) | 2.0% |
| V2-HB—C | 12.0% |
| 1V2-HB—C | 12.0% |
| 3-HB—C | 24.0% |
| 3-HB(3F)—C | 5.0% |
| 2-BTB-1 | 2.0% |
| 3-HH-4 | 8.0% |
| 3-HH—VFF | 6.0% |
| 2-HHB—C | 3.0% |
| 3-HHB—C | 6.0% |
| 3-HB(3F)TB-2 | 6.0% |

COMPOSITION EXAMPLE 17

| | |
|---|---|
| 3-B(3F)B(3,5F)B(3F)B(3F)—CL (Compound No. 49) | 1.0% |
| 2-BBB(3,5F)B(3F)—OCF$_3$ (Compound No. 10) | 1.0% |
| 3-B2B(3F)B(3,5F)B(3F)—F (Compound No. 1) | 5.0% |
| 2-HHB(3F)—F | 17.0% |
| 3-HHB(3F)—F | 17.0% |
| 5-HHB(3F)—F | 16.0% |
| 2-H2HB(3F)—F | 10.0% |
| 3-H2HB(3F)—F | 5.0% |
| 5-H2HB(3F)—F | 10.0% |
| 2-HBB(3F)—F | 6.0% |
| 3-HBB(3F)—F | 6.0% |
| 5-HBB(3F)—F | 6.0% |
| CN | 0.3 part |

COMPOSITION EXAMPLE 18

| | |
|---|---|
| 2-BBB(3,5F)B(3F)—OCF$_3$ (Compound No. 10) | 2.0% |
| 3-B2B(3F)B(3,5F)B(3F)—F (Compound No. 1) | 2.0% |
| 7-HB(3F)—F | 5.0% |
| 5-H2B(3F)—F | 5.0% |
| 3-HB—O2 | 10.0% |
| 3-HH-4 | 2.0% |
| 3-HH[5D,6D,7D]-4 | 3.0% |
| 2-HHB(3F)—F | 10.0% |
| 3-HHB(3F)—F | 10.0% |
| 5-HH[5D,6D,7D]B(3F)—F | 10.0% |
| 3-H2HB(3F)—F | 5.0% |
| 2-HBB(3F)—F | 3.0% |
| 3-HBB(3F)—F | 3.0% |
| 5-HBB(3F)—F | 6.0% |
| 2-H2BB(3F)—F | 5.0% |
| 3-H2BB(3F)—F | 6.0% |
| 3-HHB-1 | 8.0% |
| 3-HHB—O1 | 5.0% |

COMPOSITION EXAMPLE 19

| | |
|---|---|
| 4O—B(2,3F)BB(2,3F)2B-3 (Compound No. 147) | 3.0% |
| 7-HB(3,5F)—F | 3.0% |
| 3-HB—O2 | 7.0% |
| 2-HHB(3F)—F | 10.0% |
| 3-HHB(3F)—F | 10.0% |
| 5-HHB(3F)—F | 10.0% |
| 2-HBB(3F)—F | 9.0% |
| 3-HBB(3F)—F | 9.0% |
| 5-HBB(3F)—F | 16.0% |
| 2-HBB—F | 4.0% |
| 3-HBB—F | 4.0% |
| 3-HBB(3,5F)—F | 5.0% |
| 5-HBB(3,5F)—F | 10.0% |

COMPOSITION EXAMPLE 20

| | |
|---|---|
| 3-BB(3,5F)CH$_2$OBB(3,5F)—CF$_3$ (Compound No. 179) | 2.0% |
| 7-HB(3,5F)—F | 3.0% |
| 3-H2HB(3,5F)—F | 12.0% |
| 4-H2HB(3,5F)—F | 10.0% |
| 5-H2HB(3,5F)—F | 8.0% |
| 3-HHB(3,5F)—F | 5.0% |
| 4-HHB(3,5F)—F | 5.0% |
| 3-HH2B(3,5F)—F | 15.0% |
| 5-HH2B(3,5F)—F | 10.0% |
| 3-HBB(3,5F)—F | 12.0% |
| 5-HBB(3,5F)—F | 12.0% |
| 3-HBCF$_2$OB(3,5F)—F | 6.0% |

COMPOSITION EXAMPLE 21

| | |
|---|---|
| 3-B(3F)B(3,5F)B(3F)B(3F)—CL (Compound No. 49) | 1.0% |
| 2-BBB(3,5F)B(3F)—OCF$_3$ (Compound No. 10) | 2.0% |
| 3-B2B(3F)B(3,5F)B(3F)—F (Compound No. 1) | 3.0% |
| 7-HB(3,5F)—F | 5.0% |
| 3-H2HB(3,5F)—F | 12.0% |
| 4-H2HB(3,5F)—F | 8.0% |
| 3-HHB(3,5F)—F | 10.0% |
| 4-HHB(3,5F)—F | 5.0% |
| 3-HBB(3,5F)—F | 10.0% |
| 3-HHEB(3,5F)—F | 10.0% |
| 4-HHEB(3,5F)—F | 3.0% |
| 5-HHEB(3,5F)—F | 3.0% |
| 2-HBEB(3,5F)—F | 3.0% |
| 3-HBEB(3,5F)—F | 5.0% |
| 5-HBEB(3,5F)—F | 3.0% |
| 3-HD(3,5)B(3,5F)—F | 15.0% |
| 3-HHBB(3,5F)—F | 2.0% |

COMPOSITION EXAMPLE 22

| | |
|---|---|
| 3-B2B(3F)B(3,5F)B(3F)—F (Compound No. 1) | 5.0% |
| 4O—B(2,3F)BB(2,3F)2B-3 (Compound No. 147) | 3.0% |
| 3-BB(3,5F)CH₂OBB(3,5F)—CF₃ (Compound No. 179) | 2.0% |
| 3-HB—CL | 10.0% |
| 5-HB—CL | 4.0% |
| 7-HB—CL | 4.0% |
| 1O1-HH-5 | 5.0% |
| 2-HBB(3F)—F | 8.0% |
| 3-HBB(3F)—F | 8.0% |
| 5-HBB(3F)—F | 9.0% |
| 4-HHB—CL | 8.0% |
| 5-HHB—CL | 3.0% |
| 3-H2HB(3F)—CL | 4.0% |
| 3-HBB(3,5F)—F | 10.0% |
| 5-H2BB(3,5F)—F | 9.0% |
| 3-HB(3F)VB-2 | 4.0% |
| 3-HB(3F)VB-3 | 4.0% |

COMPOSITION EXAMPLE 23

| | |
|---|---|
| 2-BBB(3,5F)B(3F)—OCF₃ (Compound No. 10) | 2.0% |
| 3-HHB(3,5F)—F | 9.0% |
| 3-H2HB(3,5F)—F | 8.0% |
| 4-H2HB(3,5F)—F | 8.0% |
| 5-H2HB(3,5F)—F | 8.0% |
| 3-HBB(3,5F)—F | 21.0% |
| 5-HBB(3,5F)—F | 20.0% |
| 3-H2BB(3,5F)—F | 10.0% |
| 5-HHBB(3,5F)—F | 3.0% |
| 5-HHEBB—F | 2.0% |
| 3-HH2BB(3,5F)—F | 3.0% |
| 1O1-HBBH-4 | 4.0% |
| 1O1-HBBH-5 | 2.0% |

COMPOSITION EXAMPLE 24

| | |
|---|---|
| 3-B2B(3F)B(3,5F)B(3F)—F (Compound No. 1) | 2.0% |
| 5-HB—F | 12.0% |
| 6-HB—F | 9.0% |
| 7-HB—F | 7.0% |
| 2-HHB—OCF₃ | 7.0% |
| 3-HHB—OCF₃ | 7.0% |
| 4-HHB—OCF₃ | 7.0% |
| 5-HHB—OCF₃ | 5.0% |
| 3-HH2B—OCF₃ | 4.0% |
| 5-HH2B—OCF₃ | 4.0% |
| 3-HHB(3,5F)—OCF₃ | 5.0% |
| 3-HBB(3F)—F | 10.0% |
| 5-HBB(3F)—F | 10.0% |
| 3-HH2B(3F)—F | 3.0% |
| 3-HB(3F)BH-3 | 2.0% |
| 5-HBBH—3 | 2.0% |
| 3-HHB(3,5F)—OCF₂H | 4.0% |

COMPOSITION EXAMPLE 25

| | |
|---|---|
| 3-B(3F)B(3,5F)B(3F)B(3F)—CL (Compound No. 49) | 1.0% |
| 3-B2B(3F)B(3,5F)B(3F)—F (Compound No. 1) | 3.0% |
| 5-H4HB(3,5F)—F | 7.0% |
| 5-H4HB—OCF₃ | 15.0% |
| 3-H4HB(3,5F)—CF₃ | 8.0% |
| 5-H4HB(3,5F)—CF₃ | 10.0% |
| 3-HB—CL | 6.0% |
| 5-HB—CL | 4.0% |
| 2-H2BB(3F)—F | 5.0% |
| 3-H2BB(3F)—F | 10.0% |
| 5-HVHB(3,5F)—F | 5.0% |
| 3-HHB—OCF₃ | 3.0% |
| 3-H2HB—OCF₃ | 3.0% |
| V—HHB(3F)—F | 5.0% |
| 3-HHB(3F)—F | 5.0% |
| 5-HHEB—OCF₃ | 2.0% |
| 3-HBEB(3,5F)—F | 5.0% |
| 5-HH—V2F | 3.0% |

COMPOSITION EXAMPLE 26

| | |
|---|---|
| 2-BBB(3,5F)B(3F)—OCF₃ (Compound No. 10) | 3.0% |
| 3-B2B(3F)B(3,5F)B(3F)—F (Compound No. 1) | 3.0% |
| 2-HHB(3F)—F | 2.0% |
| 3-HHB(3F)—F | 2.0% |
| 5-HHB(3F)—F | 2.0% |
| 2-HBB(3F)—F | 6.0% |
| 3-HBB(3F)—F | 6.0% |
| 5-HBB(3F)—F | 10.0% |
| 2-H2BB(3F)—F | 9.0% |
| 3-H2BB(3F)—F | 9.0% |
| 3-HBB(3,5F)—F | 25.0% |
| 5-HBB(3,5F)—F | 19.0% |
| 1O1-HBBH-4 | 2.0% |
| 1O1-HBBH-5 | 2.0% |

COMPOSITION EXAMPLE 27

| | |
|---|---|
| 3-B(3F)B(3,5F)B(3F)B(3F)—CL (Compound No. 49) | 1.0% |
| 2-BBB(3,5F)B(3F)—OCF₃ (Compound No. 10) | 1.0% |
| 3-B2B(3F)B(3,5F)B(3F)—F (Compound No. 1) | 3.0% |
| 5-HB—CL | 12.0% |
| 3-HH-4 | 7.0% |
| 3-HB—O2 | 20.0% |
| 3-H2HB(3,5F)—F | 8.0% |
| 3-HHB(3,5F)—F | 8.0% |
| 3-HBB(3,5F)—F | 6.0% |
| 2-HHB(3F)—F | 5.0% |
| 3-HHB(3F)—F | 5.0% |
| 2-H2HB(3F)—F | 2.0% |
| 3-H2HB(3F)—F | 1.0% |
| 5-H2HB(3F)—F | 2.0% |
| 3-HHBB(3,5F)—F | 4.0% |
| 3-HBCF₂OB—OCF3 | 4.0% |
| 5-HBCF₂OB(3,5F)—CF₃ | 4.0% |
| 3-HHB-1 | 3.0% |
| 3-HHB—O1 | 4.0% |

COMPOSITION EXAMPLE 28

| | |
|---|---|
| 3-B(3F)B(3,5F)B(3F)B(3F)—CL (Compound No. 49) | 1.0% |
| 2-BBB(3,5F)B(3F)—OCF₃ (Compound No. 10) | 1.0% |
| 3-B2B(3F)B(3,5F)B(3F)—F (Compound No. 1) | 20.0% |
| 4O—B(2,3F)BB(2,3F)2B-3 (Compound No. 147) | 3.0% |
| 3-BB(3,5F)CH₂OBB(3,5F)—CF₃ (Compound No. 179) | 2.0% |
| 2-HHB(3F)—F | 17.0% |
| 3-HHB(3F)—F | 17.0% |
| 5-HHB(3F)—F | 4.0% |
| 2-H2HB(3F)—F | 10.0% |
| 3-H2HB(3F)—F | 5.0% |
| 5-H2HB(3F)—F | 5.0% |
| 2-HBB(3F)—F | 6.0% |

-continued

| | |
|---|---|
| 3-HBB(3F)—F | 6.0% |
| 5-HBB(3F)—F | 3.0% |

COMPOSITION EXAMPLE 29

| | |
|---|---|
| 2-BBB(3,5F)B(3F)—OCF$_3$ (Compound No. 10) | 1.0% |
| 3-B2B(3F)B(3,5F)B(3F)—F (Compound No. 1) | 5.0% |
| 4O—B(2,3F)BB(2,3F)2B-3 (Compound No. 147) | 2.0% |
| 3-BB(3,5F)CH$_2$OBB(3,5F)—CF$_3$ (Compound No. 179) | 2.0% |
| 3-BEB(3F)—C | 8.0% |
| 3-HB—C | 8.0% |
| V—HB—C | 8.0% |
| 1V—HB—C | 8.0% |
| 3-HB—O2 | 3.0% |
| 3-HH-2V | 14.0% |
| 3-HH-2V1 | 7.0% |
| V2-HHB-1 | 10.0% |
| 3-HHB-1 | 5.0% |
| 3-HHEB—F | 7.0% |
| 3-H2BTB—2 | 6.0% |
| 3-H2BTB-3 | 6.0% |

COMPOSITION EXAMPLE 30

| | |
|---|---|
| 3-B(3F)B(3,5F)B(3F)B(3F)—CL (Compound No. 49) | 1.0% |
| 2-BBB(3,5F)B(3F)—OCF$_3$ (Compound No. 10) | 2.0% |
| 3-B2B(3F)B(3,5F)B(3F)—F (Compound No. 1) | 2.0% |
| 3-H2HB(3,5F)—F | 7.0% |
| 5-H2HB(3,5F)—F | 8.0% |
| 3-HHB(3,5F)—F | 10.0% |
| 4-HHB(3,5F)—F | 5.0% |
| 3-HH2B(3,5F)—F | 9.0% |
| 5-HH2B(3,5F)—F | 4.0% |
| 3-HBB(3,5F)—F | 15.0% |
| 5-HBB(3,5F)—F | 15.0% |
| 3-HBEB(3,5F)—F | 2.0% |
| 4-HBEB(3,5F)—F | 2.0% |
| 5-HBEB(3,5F)—F | 2.0% |
| 3-HHEB(3,5F)—F | 10.0% |
| 4-HHEB(3,5F)—F | 3.0% |
| 5-HHEB(3,5F)—F | 3.0% |

COMPOSITION EXAMPLE 31

| | |
|---|---|
| 4O—B(2,3F)BB(2,3F)2B-3 (Compound No. 147) | 3.0% |
| 3-HH-5 | 5.0% |
| 3-HH-4 | 5.0% |
| 3-HH—O1 | 6.0% |
| 3-HH—O3 | 6.0% |
| 3-HB—O1 | 5.0% |
| 3-HB—O2 | 5.0% |
| 3-HB(2,3F)—O2 | 10.0% |
| 5-HB(2,3F)—O2 | 10.0% |
| 3-HHB(2,3F)—O2 | 12.0% |
| 5-HHB(2,3F)—O2 | 13.0% |
| 3-HHB(2,3F)-2 | 4.0% |
| 5-HHB(2,3F)-1 | 4.0% |
| 3-HHEH-3 | 5.0% |
| 3-HHEH-5 | 5.0% |
| 4-HHEH-3 | 2.0% |

BEST MODE FOR CARRYING OUT THE INVENTION

Now, the present invention will be described in more detail with reference to Examples. In each of the Examples, C indicates crystal, SA: smectic phase A, SB: smectic phase B, SX: smectic phase the structure of which has not yet been defined, N: nematic phase, and Iso: isotropic phase, and the unit of all phase transition temperatures is °C.

EXAMPLE 1

Preparation of 2",2',6',3,4-pentafluoro-4"-(2-(4-propylphenyl)ethyl)terphenyl (3-B2B(3F)B(3,5F)B(3F)-F (Compound No. 1))

(First step) Preparation of 3-fluoro-4'-propyldeoxybenzoin

In a mixture of 48.9 g (248.8 imol) of (4-propylphenyl) acetylchloride, 2.6 g (7.5 mmol) of tris(2,4-pentanedionata) iron (III), and 200 ml of toluene was added dropwise a solution of a Grignard reagent prepared from 56.6 g (323.5 mmol) of 1-bromo-3-fluorobenzene and 8.2 g (335.9 mmol) of Mg in 300 ml of tetrahydrofuran (THF) while maintaining them at a temperature lower than −60° C. After finishing of the dropping, they were stirred at the same temperature for 3 hours. Subsequently, the reaction mixture was raised up to room temperature, 200 ml of a diluted hydrochloric acid was added dropwise thereto, and then extracted with 150 ml of heptane. The organic layer thus obtained was washed with an aqueous sodium bicarbonate solution thrice and with water thrice, and then dried over anhydrous magnesium sulfate. After the solvent was distilled off under a reduced pressure, the residue was subjected to silica gel column chromatography (eluent: toluene/heptane=8/2) to obtain 43.3 g of a crude 3-fluoro-4'-propyldeoxybenzoin. This product was recrystallized from methanol to obtain 28.5 g of the subject compound. (Yield: 44.8%)

(Second step) Preparation of 3-fluoro-(2-(4-propylphenyl) ethyl)benzene

After 28 ml (175.6 mol) of triethylsilane was added dropwise to a solution of 15.0 g (58.5 mmol) of the 3-fluoro-4'-propyldeoxybenzoin obtained in the previous step in 40 ml of trifluoroacetic acid while being cooled with ice, they were stirred at room temperature for 3 hours.

The reaction solution was extracted with 150 ml of heptane, and the organic layer thus obtained was washed with an aqueous sodium bicarbonate solution thrice and with water thrice, and then dried over anhydrous magnesium sulfate. After the solvent was distilled off under a reduced pressure, the residue was subjected to silica gel column chromatography (eluent: heptane) to obtain 4.8 g of a crude 3-fluoro-(2-(4-propylphenyl)ethyl)benzene. This product was used for next reaction without any further purification. (Yield: 33.9%)

(Third step) Preparation of 3-fluoro-4-iodo-(2-(4-propylphenyl)ethyl)benzene

In a solution of 4.8 g (19.7 mmol) of the 3-fluoro-(2-(4-propylphenyl)ethyl)benzene obtained in the previous step in 25 ml of THF was added dropwise 23 ml of sec-BuLi (1.04 M, cyclohexane solution, corresponding to 23.7 mmol) while being maintained at a temperature lower than −60° C., and they were stirred at the same temperature for 1 hour. Subsequently, a solution of 7.5 g (29.6 mmol) of iodine in 20 ml of THF was added dropwise to the reaction mixture while being maintained at a temperature lower than −60° C., and they were stirred at the same temperature for 1 hour. The reaction solution was poured into 50 ml of a diluted aqueous sodium thiosulfate solution, and extracted with 50 ml of heptane. The organic layer thus obtained was washed with water thrice and then dried over anhydrous magnesium sulfate. After the solvent was distilled off under a reduced pressure, the residue was subjected to silica gel column chromatography (eluent: heptane) to obtain 6.5 g of a crude 3-fluoro-4-iodo-(2-(4-propylphenyl)ethyl)benzene. This product was used for next reaction without any further purification. (Yield: 90.2%)

(Fourth step) Preparation of 4'-(2-(4-propylphenyl)ethyl)-2',3,5-trifluorobiphenyl A mixture of 6.5 g (17.7 mmol) of the 3-fluoro-4-iodo(2-(4-propylphenyl)ethyl)benzene obtained in the previous step, 3.8 g (26.5 mmol) of dihydroxy(3,5-difluorophenyl)borane, 4.9 g (35.3 mmol) of potassium carbonate, 0.5 g of palladium carried on carbon (5%), and 50 ml of toluene/ethanol/water (1/1/1) was heated to reflux for 15 hours. The catalyst was removed by filtration, the mixture was subjected to extraction with 250 ml of toluene, the organic layer thus obtained was washed with water thrice, and then dried over anhydrous magnesium sulfate. The solvent was distilled off under a reduced pressure and the residue thus obtained was subjected to silica gel column chromatography (eluent: heptane/toluene=9/1) to obtain 5.2 g of a crude 4'-(2-(4-propylphenyl)ethyl)-2',3,5-trifluorobiphenyl. This product was used for next reaction without any further purification. (Yield: 87.8%)

(Fifth step) Preparation of 4'-(2-(4-propylpheny)ethyl)-2',3,5-trifluoro-4-iodobiphenyl The same procedures as in the third step were repeated with the exception that 5.2 g (15.5 mmol) of the 4'-(2-(4-propylphenyl)ethyl)-2',3,5-trifluorobiphenyl obtained in the fourth step was used in place of the 3-fluoro-(2-(4-propylphenyl)ethyl)benzene used in the third step, and that 14 ml of n-BuLi (1.66M, THF solution, corresponding to 23.3 mmol) was used in place of sec-BuLi, to obtain 4.3 g of 4'-(2-(4-propylphenyl)ethyl)-2',3,5-trifluoro-4-iodobiphenyl. (Yield: 57.4%)

(Sixth step) Preparation of 2",2',5',3,4-pentafluoro-4"-(2-(4-propylphenyl)ethyl)terphenyl The same procedures as in the fourth step were repeated with the exception that 4.3 g (8.9 mmol) of the 4'-(2-(4-propylphenyl)ethyl)-2',3,5-trifluoro-4-iodobiphenyl obtained in the fifth step was used in place of the 3-fluoro-4-iodo-(2-(4-propylphenyl)ethyl)benzene used in the fourth step, and that 2.1 g (13.3 mmol) of dihydroxy(3,4-difluorophenyl)borane was used in place of dihydroxy(3,5-difluorophenyl)borane, to obtain 3.4 g of a crude 2",2',6',3,4-pentafluoro-4"-(2-(4-propylphenyl)ethyl)terphenyl. This product was recrystallized from mixed solvent of ethanol/ethyl acetate (8/2) to obtain 2.6 g of the subject compound. (Yield: 62.3%) Phase transition temperatures of this product were as follows:

C 112.5~113.9 N 118.3~118.5 Iso

Further, the data of each of the spectrums well supported its structure.

Mass analysis: 466 (M+)

$_1$H-NMR (CDCl$_3$, TMS internal standard)

δ (ppm)

0.94 (t, 3H)

1.67 (tq, 2H)

2.57 (t, 2H)

2.94 (s, 4H)

6.94–7.44 (m, 12H)

Examples in which the compounds of the present invention were used as component of liquid crystal compositions are shown below. In each of the Use Examples, NI means phase transition temperature (° C.) of nematic phase-isotropic phase, A E: dielectric anisotropy value, An: optical anisotropy value, η: viscosity (mPa·s), Vth: threshold voltage (V), P: pitch (μm) of twist, and VHR: voltage holding ratio (%).

In this connection, η was determined at 20° C.; Δε, Δn, Vth, and P were determined at 25° C., respectively; and VHR indicates the value determined at 25° C., 80° C., or 100° C. from the left hand side in turn.

EXAMPLE 2

(Use Example 1)

Liquid crystal composition (A) comprising the following cyanophenylcyclohexane type liquid crystalline compounds in the amount shown below

| | |
|---|---|
| 4-(trans-4-propylcylohexyl) benzonitrile | 24% |
| 4-(trans-4-pentylcylohexyl) benzonitrile | 36% |
| 4-(trans-4-heptylcylohexyl) benzonitrile | 25% |
| 4-(trans-4-pentylcylohexyl)-4'-cyanobiphenyl | 15% | had the following physical properties:

NI: 71.7, Δε 10.0, Δn 0.137, η: 26.7, Vth:1.78

Liquid crystal composition (B) comprising 85% of the composition (A) and 15% of the 2",2',6',3,4-pentafluoro-4"-(2-(4-propylphenyl)ethyl)terphenyl (Compound No. 1) obtained in Example 1 had the following physical properties:

NI: 75.2, Δε 11.3, Δn 0.149, η:35.6, Vth:1.71

While this liquid crystal composition (B) was allowed to stand in a freezer at –20° C., development of smectic phase or separation of crystals was not observed.

According to a method similar to that of Example 1, the following compounds (Compound Nos. 2 through 174) can be synthesized: (In the following, Compound No. is abbreviated to Cpd. No.)

Cpd. No. 2: 1-B(3,5F)B(3F)BB-F
Cpd. No. 3: 2-B(3,5F)BB(3F)B-CF$_3$
Cpd. No. 4: 3-B(3,5F)BBB(3F)-CF$_2$H
Cpd. No. 5: 4-B(3F)B(3,5F)BB-CFH$_2$
Cpd. No. 6: 5-BB(3,5F)B(3F)B-OCF$_3$
Cpd. No. 7: 6-BB(3,5F)BB(3F)-OCF$_2$H
Cpd. No. 8: 7-B(3F)BB(3,5F)B-OCF$_2$CF$_2$H
Cpd. No. 9: 8-BB(3F)B(3,5F)B-OCF$_2$CFHCF$_3$
Cpd. No. 10: 2-BBB(3; 5F)B(3F)-OCF$_3$ NI: 74.1, Δε 11.3, Δn 0.139, κ: 27.6
Cpd. No. 11: 3O-BBB(3,5F)B(3F)-OCF$_2$CH$_2$CF$_3$
Cpd. No. 12: 3O-B(3F)BBB(3,5F)-F
Cpd. No. 13: 1O5-BB(3F)BB(3,5F)-CL
Cpd. No. 14: 18-BBB(3F)B(3,5F)-CF$_3$
Cpd. No. 15: 13O-B(3F)B(3F)B(3F)B-CF$_2$H
Cpd. No. 16: 1O3O-B(3F)BB(3F)B(3F)-CFH$_2$
Cpd. No. 17: 1-BB(3F)B(3F)B(3F)-OCF$_3$
Cpd. No. 18: 2-B(3F)B(3F)BB(3F)-OCF$_2$H
Cpd. No. 19: 3-B(3,5F)B(3,5F)BB-CF$_2$CF$_2$H
Cpd. No. 20: 4-B(3,5F)BB(3,5F)B-CF$_2$CFHCF$_3$
Cpd. No. 21: 5-B(3,5F)BBB(3,5F)-CF$_2$CH$_2$CF$_3$
Cpd. No. 22: 6-B 3,5F)B(3F)B(3F)B-CL
Cpd. No. 23: 7-B(3,5F)B(3F)BB(3F)-F
Cpd. No. 24: 8-B(3,5F)BB(3F)B(3F)-CF$_3$
Cpd. No. 25: 9-BB(3,5F)B(3,5F)B-CF$_2$H
Cpd. No. 26: 1 9-BB(3,5F)BB(3,5F)B-CF$_2$H
Cpd. No. 27: 3-B(3F)B(3,5F)B(3F)B-OCF$_3$
Cpd. No. 28 3-B(3F)B(3,5F)B(3F)B-OCF$_2$H
Cpd. No. 29: 3-BB(3,5F)B(3F)B(3F)-C $_2$F$_5$
Cpd. No. 30: 2-BBB(3,5F)B(3,5F)-F
Cpd. No. 31: 2-B(3F)B(3F)B(3,5F)B-CL
Cpd. No. 32: 5-B(3F)BB(3,5F)B(3F)-CF$_3$
Cpd. No. 33: 5-BB(3F)B(3,5F)B(3-F)-CF$_2$H
Cpd. No. 34 5-B(3F)B(3F)BB(3,5F)-CFH$_2$
Cpd. No. 35: 4-B(3F)BB(3F)B(3,5F)-OCF$_3$
Cpd. No. 36: 4-BB(3F)B(3F)B(3,5F)-OCF$_2$H
Cpd. No. 37: 4-B(3F)B(3F)B(3F)B(3F)-OCF$_2$ CF$_2$H

Cpd. No. 38: 3-B(3,5F)B(3,5F)B(3F)B-F
Cpd. No. 39: 3-B(3,5F)B(3,5F)BB(3F)-CL
Cpd. No. 40: 3-B(3,5F)B(3F)B(3,5F)B-CF$_3$
Cpd. No. 41: 3-B(3,5F)BB(3,5F)B(3F)-CF$_2$H
Cpd. No. 42: 3-B(3,5F)B(3F)BB(3,5F)-CFH$_2$
Cpd. No. 43: 4-B(3,5F)BB(3F)B(3,5F)-OCF$_3$
Cpd. No. 44: 4-B(3,5F)B(3F)B(3F)B(3F)-OC F$_2$H
Cpd. No. 45: 4-B(3F)B(3,5F)B(3,5F)B-OCF$_2$ CFHCF$_3$
Cpd. No. 46: 4-BB(3,5F)B(3F)B(3F)-F
Cpd. No. 47: 4-B(3F)B(3,5F)BB(3,5F)-CL
Cpd. No. 48: 5O-BB(3,5F)B(3F)B(3,5F)-CF$_3$
Cpd. No. 49: 3-B(3F)B(3,5F)B(3F)B(3F)-CL NI: 72.1, Δε 11.2, Δn 0.139, η: 26.6
Cpd. No. 50: 2-B(3F)B(3,5F)B(3F)B(3F)-F
Cpd. No. 51: 2-B(3F)BB(3,5F)B(3,5F)-CL
Cpd. No. 52: 2-BB(3F)B(3,5F)B(3,5F)-CF$_3$
Cpd. No. 53 1-B(3F)B(3F)B(3,5F)B(3F)-CF$_2$H
Cpd. No. 54: 2-B(3F)B(3F)B(3F)B(3,5F)-CF H$_2$
Cpd. No. 55: 3-B(3,5F)B(3,5F)B(3F)B(3F)—OCF$_3$
Cpd. No. 56: 5-B(3,5F)B(3F)B(3,5F)B(3F)—OCF$_2$H
Cpd. No. 57: 5-B(3,5F)B(3F)B(3F)B(3,5F)—F
Cpd. No. 58 5-BB(3,5F)B(3,5F)B(3,5F)-CL
Cpd. No. 59: 5-B(3F)B(3,5F)B(3,5F)B(3F)—OCF$_2$CH$_2$CF$_3$
Cpd. No. 60: 6-B(3F)B(3F)B(3,5F)B(3,5F)—CF$_3$
Cpd. No. 61: 6-B(3,5F)B(3,5F)B(3,5F)B(3,5F)-CF$_2$H
Cpd. No. 62: 3-B(3,5F)BB(3F)B-1
Cpd. No. 63: 3-BBB(3,6F)B(3F)-O5
Cpd. No. 64: 5-BB(3,6F)BB(2F)-10
Cpd. No. 65: 5-BB(3F)B(2,5F)B-3
Cpd. No. 66: 4O-B(2F)BBB(3F)-O2
Cpd. No. 67: 18-BB(3F)B(2,3F)B-12
Cpd. No. 68: 5-B(3F)BB(2,3F)B-2
Cpd. No. 69: 4-BB(3,5F)B(3F)B(3F)-1
Cpd. No. 70: 3-B(3F)B(3,6F)BB(3F)-3
Cpd. No. 71: 3O-B(2,3F)BB(2,3F)B-2
Cpd. No. 72: 5-BB(2,3F)B(2,3F)B-5
Cpd. No. 73: 5-BB(3,6F)BB(2,3F)-1
Cpd. No. 74: 7-B(3,5F)BB(3,5F)B(3F)-3
Cpd. No. 75: 3O1-B(2,3F)BB(2F)B(2,3F)-2
Cpd. No.76: 1O5-BB(2,3F)B(2,3F)B(2F)-1
Cpd. No. 77: 1O2O-B(3,5F)B(3F)B(3F)B(3,5F)— 2
Cpd. No. 78: 2-BB(2,3F)B(3,6F)B(2,3F)-1
Cpd. No. 79: 3-B(2,5F)B(2,3F)BB(2,3F)-3
Cpd. No. 80: 3-B(2,3F)BB(2,3F)B(2,3F)-4
Cpd. No. 81: 5-B(2,3F)B(2,3F)B(2,3F)B(2,3F)-3
Cpd. No. 82: 1-B(3,5F)2B(3F)BB-F
Cpd. No. 83: 2-B(3F)2B(3,5F)BB-CL
Cpd. No. 84: 3-B(3F)2BB(3,5F)B-CF$_3$
Cpd. No. 85: 4-B(3F)2BBB(3,5F)-OCF$_3$
Cpd. No. 86: 5-B(3F)2B(3F)B(3F)B-OCF$_2$H
Cpd. No. 87: 6-B(3F)2BB(3F)B(3F)-CF$_2$H
Cpd. No. 88: 7-B(3,5F)2BB(3,5F)B-OCF$_2$CF$_2$H
Cpd. No. 89: 8-B(3,5F)2B(3F)BB(3F)-OCF$_2$C FHCF$_3$
Cpd. No. 90: 5O-B2B(3,5F)BB(3F)-F
Cpd. No. 91: 2O2-B2B(3,5F)B(3F)B(3F)-CL
Cpd. No. 92: 3-B(3F)2BB(3F)B(3F)-CF$_3$
Cpd. No. 93: 3-B(3F)2BB(3F)B(3,5F)-OCF$_2$H
Cpd. No. 94: 4-B(3,5F)2B(3,5F)BB(3F)-OCF$_3$
Cpd. No. 95: 4-B(3,5F)2BB(3,5F)B(3F)-CF$_2$H
Cpd. No. 96: 5-B(3F)2B(3,5F)B(3F)B(3F)-CF$_2$H
Cpd. No. 97: 5-B(3F)2BB(3,5F)B(3,5F)-CL
Cpd. No. 98: 6-B(3F)2B(3F)B(3F)B(3,5F)-CFH$_2$
Cpd. No. 99: 2O1O-B(3F)2B(3,5F)B(3,5F)B (3F)-CF$_3$
Cpd. No. 100: 1-B2B(3F)B(3,5F)B-2
Cpd. No. 101: 2-B(2,3F)2B(3F)BB-3
Cpd. No. 102: 3-B2B(3F)B(2,3F)B-4
Cpd. No. 103: 5-B(3F)2B(3,5F)B(3,5F)B-1

Cpd. No. 104: 5-B2B(3,6F)B(2F)B(2,3F)-O2
Cpd. No. 105: 4O-B(2,3F)2B(3,6F)BB(2,3F)—O1
CpC. No. 106: 7-B(3,5F)B2B(3F)B-F
Cpd. No. 107: 6-BB(3,5F)2B(3F)B-CL
Cpd. No. 108: 5-BB(3F)2B(3,5F)B-CF$_3$
Cpd. No. 109: 4-BB(5F)2BB(3,5F)-OCF$_3$
Cpd. No. 110: 3-B(3F)B(3F)2BB(3F)-CF$_2$H
Cpd. No. 111: 2-B(3,5F)B(3,5F)2BB-OCF$_2$CH$_2$ CF$_2$
Cpd. No. 112: 1O-B(3,5F)B2BB(3,5F)-F
Cpd. No. 113: 2O1-B(3,5F)B2B(3F)B(3F)-CL
Cpd. No. 114: 5-B(3F)B(3,5F)2B(3F)B-OCF$_3$
Cpd. No. 115: 4-BB(3F)2B(3,5F)B(3F)-CF$_2$H
Cpd. No. 116: 2-BB(3F)2B(3F)B(3,5F)-CFH$_2$
Cpd. No. 117: 3-B(3,5F)B(3F)2B(3F)B(3F)—F
Cpd. No. 118: 3-B(3F)B(3,5F)2B(3,5F)B-F
Cpd. No. 119: 6-B(3F)B(3,5F)2BB(3,5F)-CL
Cpd. No. 120: 5-BB(3F)2B(3,5F)B(3,5F)-OC F$_2$H
Cpd. No. 121: 4-B(3F)B(3,5F)2B(3,5F)B(3 F)-CF$_3$
Cpd. No. 122: 2-B(3,5F)B(3,5F)2B(3,5F)B (3,5F)-CFH$_2$
Cpd. No. 123: 4O-BB2B(3,6F)B(2F)-O2
Cpd. No. 124: 3-BB(3,5F)2B(3F)B(3F)-O4
Cpd. No. 125: 4-BB(2,3F)2B(2F)B(2F)-3
Cpd. No. 126: 5-BB(3,6F)2B(3,6F)B(2F)-2
Cpd. No. 127: 5-BB(3,5F)2B(3,5F)B(3F)-3
Cpd. No. 128: 4-B(2F)B(2,3F)2B(2,3F)B(3 F)-2
Cpd. No. 129: 1-B(3,5F)BB2B(3F)-F
Cpd. No. 130: 3-BB(3,5F)B2B(3F)-CL
Cpd. No. 131: 5-BBB(3,5F)2B(3F)-CF$_3$
Cpd. No. 132: 7-BBB(3F)2B(3,5F)-OCF$_3$
Cpd. No. 133: 9-BB(3F)B(3F)2B(3F)-OCF$_2$H
Cpd. No. 134: 6O-B(3,5F)BB(3,5F)2B-F
Cpd. No. 135: 5O1-B(3,5F)B(3F)B(3F)2B-OC F$_2$CF$_2$H
Cpd. No. 136: 1O4-BB(3,5F)B(3,5F)2B-OCF$_2$CFHCF$_3$
Cpd. No. 137: 1O2O-B(3F)B(3,5F)B2B(3F)-OCF$_2$H
Cpd. No. 138: 15O-B(3F)B(3F)B(3,5F)2B-OCF$_3$
Cpd. No. 139: 3-B(3F)B(3F)B2B(3,5F)-CF$_3$
Cpd. No. 140: 3-B(3,5F)B(3,5F)B(3F)2B-F
Cpd. No. 141: 5-B(3,5F)B(3F)B(3,5F)2B-CL
Cpd. No. 142: 4-BB(3,5F)B(3,5F)2B(3F)-CF$_3$
Cpd. No. 143: 2-BB(3,5F)B(3F)2B(3,5F)-OC F$_3$
Cpd. No. 144: 6-B(3F)B(3F)B(3,5F)2B(3F)—CF$_2$H
Cpd. No. 145: 3-B(3F)B(3,5F)B(3F)2B(3,5 =F)-CF$_2$H
Cpd. No. 146: 3-BBB(3F)2B(2,3F)-O1
Cpd. No. 147: 4O-B(2,3F)BB(2,3F)2B-3
Cpd. No. 148: 5-BB(2,3F)B(3,6F)2B-1
Cpd. No. 149: 3O-B(2,3F)B(2,3F)B2B(3F)-O4
Cpd. No. 150: 6-B(2,3F)BB(2,3F)2B(2,3F)—3
Cpd. No. 151: 3-BB(2,3F)B(2,3F)2B(2,5F)—O7
Cpd. No. 152: 3-B4B(3F)B(3,5F)B-F
Cpd. No. 153: 4-B4B(3,5F)B(3F)B(3F)-CL
Cpd. No. 154: 5-B(3,5F)4-B(3,5F)B(3F)B-OC F$_3$
Cpd. No. 155: 3O-B(3F)4B(3,5F)B(3F)B(3F)—OCF$_3$
Cpd. No. 156: 5-B(2F)4BBB(2,3F)-O1
Cpd. No. 157: 5-B(2,3F)4BBB(2,3F)-3
Cpd. No. 158: 6-B(2,3F)4B(3F)BB(2,3F)-F
Cpd. No. 159: 3O-B(2,5F)4B(2,3F)BB(3,6F)—3
Cpd. No. 160: 5-BB(3,5F)4BB(3F)-CL
Cpd. No. 161: 3-B(3F)B(3F)4B(3F)B(3F)-OC F$_2$H
Cpd. No. 162: 2-BB(3F)4B(3,5F)B(3,5F)-C F$_2$H
Cpd. No. 163: 4-B(3F)B(3,5F)4B(3,5F)B-CF H$_2$
Cpd. No. 164: 3-BB4B(3,6F)B(2F)-2
Cpd. No. 165: 5-BB(3,6F)4B(2,5F)B-5
Cpd. No. 166: 2-BB(2,5F)4B(3,6F)B(3F)-1
Cpd. No. 167: 5-B(2,3F)B4B(2,3F)B(2,3F)-O2
Cpd. No. 168: 2-B(3,5F)BB(3F)4B-CL
Cpd. No. 169: 3-BBB(3,5F)4B(3,5F)-F
Cpd. No. 170: 6-B(3F)BB(3,5F)4B(3,5F)-OC F$_3$

Cpd. No. 171: 5O-BB(2,3F)B(3F)4B-3
Cpd. No. 172: 3O-B(2F)BB(2,3F)4B(5F)-3
Cpd. No. 173: 4-BB(2,3F)B(2,3F)4B(3F)-3
Cpd. No. 174: 5-BB(3,6F)B(3,6F)4B(3,6F)—2

EXAMPLE 3

Preparation of 2",5",2'-trifluoro-4-trifluoromethyl-4"-((4-pentyloxyphenyl)methoxy)terphenyl(5O-BCH$_2$OB(3,5F)B(3F)B—CF$_3$ (Compound No. 175))

To a mixture of 0.7 g (corresponding to 162.9 mmol) of NaH (60%) and 5 ml of dimethyl formamide (DMF) was added dropwise a solution of 5.0 g (135.8 mmol) of 2",5",2'-trifluoro-4-trifluoromethyl-4"-hydroxyterphenyl in 60 ml of DMF at room temperature. After finishing of the dropping, they were stirred for 1 hour. Subsequently, a solution of 6.2 g (203.6 mmol) of 1-iodomethyl-4-pentyloxybenzene in 30 ml of DMF was added dropwise thereto at room temperature. After finishing of the dropping, they were stirred for 3 hours. The mixture thus formed was poured into 150 ml of a diluted hydrochloric acid and extracted with 100 ml of toluene. The organic layer thus obtained was washed with an aqueous sodium bicarbonate solution and water, and then dried over anhydrous magnesium sulfate. The solvent was distilled off under a reduced pressure, and the residue thus obtained was subjected to silica gel column chromatography (eluent: heptane/toluene= 1/1) to obtain a crude 2",5"-2'-trifluoro-4-trifluoromethyl-4"-((4-pentyloxyphenyl)methoxy)terphenyl. This product was recrystallized from mixed solvent of ethanol/ethyl acetate (8/2) to obtain the subject compound.

According to a method similar to that of Example 3, the following compounds (Compound Nos. 176 through 214) can be prepared:

Cpd. No. 176:2-BB(3F)CH$_2$OBB(3,5F)-CL
Cpd. No. 177: 2-BB(3F)B(3F)CH$_2$OB(3F)-CF$_3$
Cpd. No. 178: 5-BCH$_2$OB(3F)B(3,5F)B(3F)-F
Cpd. No. 179: 3-BB(3,5F)CH$_2$OBB(3,5F)-CF$_3$
Cpd. No. 180: 2-B(3F)B(3F)B(3F)CH$_2$OB(3F)—OCF$_3$
Cpd. No. 181: 3-B(3,5F)CH$_2$OB(3F)B(3,5F)B—OCF$_3$
Cpd. No. 182: 4-B(3F)B(3F)CH$_2$OB(3F)B(3,5F)-OCF$_2$CFHCF$_3$
Cpd. No. 183: 3-BB(3,5F)B(3,5F)CH$_2$OB(3F)—OCF$_2$H
Cpd. No. 184: 4-BCH$_2$OB(3,5F)B(3,5F)B(3,5 F)-OCF$_2$H
Cpd. No. 185: 5-B(3F)B(3,5F)CH$_2$OB(3F)B(3,5F)-CF$_2$H
Cpd. No. 186: 15-B(3,5F)B(3F)B(3,5F)CH$_2$OB(3F)-F
Cpd. No. 187: 2O-BCH$_2$OB(2F)BB(2,3F)-2
Cpd. No. 188: 3-BCH$_2$OB(2F)B(3,6F)B(3F)-5
Cpd. No. 189: 5-B(2F)CH$_2$OB(2F)B(3,6F)B(2 F)-4
Cpd. No. 190: 6-B(2,3F)CH$_2$OB(2F)B(2F)B(2,3 F)-1
Cpd. No. 191: 7-BB(3F)B(3F)CH$_2$OB(2F)-2
Cpd. No. 192: 4O-B(2,3F)BBCH$_2$OB(2,3F)-O1
Cpd. No. 193: 4-B(2F)B(3F)B(3F)CH$_2$OB(2,3 F)-O2
Cpd. No. 194: 2-BOCH$_2$B(3,5F)B(3F)B-CF$_3$
Cpd. No. 195: 3-BB(3,5F)OCH$_2$B(3F)B(3F)-F
Cpd. No. 196: 4-BB(3,5F)B(3F)OCH$_2$B(3,5F)— OCF$_3$
Cpd. No. 197: 2-BC$_3$H$_6$OB(3F)B(3,5F)B-CL
Cpd. No. 198: 3-B(3F)C$_3$H$_6$OB(3,5F)B(3F)B-OCF$_2$H
Cpd. No. 199: 3-B(3F)C$_3$H$_6$OB(3,5F)B(3F)B(3F)-CF$_3$
Cpd. No. 200: 3-B(3F)C$_3$H$_6$OB(3,5F)B(3F)B(3,5F)-F
Cpd. No. 201: 5-BC$_3$H$_6$OB(2F)B(3,6F)B-3
Cpd. No. 202: 4-BB(3,5F)C$_3$H$_6$OBB(3F)-CF$_2$H
Cpd. No. 203: 6-BB(3F)C$_3$H$_6$OB(3,5F)B(3F)-O CF$_3$
Cpd. No. 204: 7-B(3F)B(3F)C$_3$H$_6$OB(3,5F)B(3 F)-F
Cpd. No. 205: 3-B(2,3 F)BC$_3$H$_6$OB(2F)B(3F)-1
Cpd. No. 206: 5-B(2,3F)BC$_3$H$_6$OB(2,3F)B(2,3F)-O$_2$
Cpd. No. 207: 5-BB(3F)BC$_3$H$_6$OB(3,5F)-CL
Cpd. No. 208: 5-BB (3F)B(3F)C$_3$H$_6$OB(3,5F)-OCF$_3$
Cpd. No. 209: 3-B(3,5F)BB(3F)C$_3$H$_6$OB(3,5F)—OCF$_2$H
Cpd. No. 210: 3-B(2F)B(3,6F)BC$_3$H$_6$OB(2,3F)—O1
Cpd. No. 211: 3-BOC$_3$H$_6$B(3,5F)BB(3F)-CF$_3$
Cpd. No. 212: 5-B(3F)B(3F)OC$_3$H$_6$B(3F)B(3F)—CF$_3$
Cpd. No. 213: 5-B-(2,5F)BB(2,3F)OC$_3$H$_6$B(3F)
Cpd. No. 214: 3-B(2F)B(2,3,F)OC$_3$H$_6$BB(2,3 F)—O4

EXAMPLE 4

(Use Example 2)

Physical properties of the liquid crystal composition of Composition Example 1 were as follows:

NI: 90.7, Δε: 7.5, Δn: 0.165, μ:15.2, Vth: 2.05, P: 11 μm

While this liquid crystal composition was allowed to stand in a freezer at —20° C., development of smectic phase or separation of crystals was not observed.

EXAMPLE 5

(Use Example 3)

Physical properties of the liquid crystal composition of Composition Example 2 were as follows:

NI: 88.6, Δε: 9.1, Δn: 0.153, η: 17.8, Vth: 1.94

While this liquid crystal composition was allowed to stand in a freezer at –20° C., development of smectic phase or separation of crystals was not observed.

EXAMPLE 6

(Use Example 4)

Physical properties of the liquid crystal composition of Composition Example 3 were as follows:

NI: 90.3, Δε: 31.6, Δn: 0.149, η: 88.5, Vth: 0.85

While this liquid crystal composition was allowed to stand in a freezer at –20° C., development of smectic phase or separation of crystals was not observed.

EXAMPLE 7

(Use Example 5)

Physical properties of the liquid crystal composition of Composition Example 4 were as follows:

NI: 94.7, Δε: 7.1, Δn: 0.206, η: 35.91 Vth: 2.13

While this liquid crystal composition was allowed to stand in a freezer at –20° C., development of smectic phase or separation of crystals was not observed.

EXAMPLE 8

(Use Example 6)

Physical properties of the liquid crystal composition of composition Example 5 were as follows:

NI: .66.4, Δε: 11.7, Δn: 0.120, η: 39.3, Vth: 1.28

While this liquid crystal composition was allowed to stand in a freezer at –20° C., development of smectic phase or separation of crystals was not observed.

EXAMPLE 9

(Use Example 7)

Physical properties of the liquid crystal composition of composition Example 6 were as follows:

NI: 77.5, Δε: 9.1, Δn: 0.142, η: 21.7, Vth: 1.63

While this liquid crystal composition was allowed to stand in a freezer at –20° C., development of smectic phase or separation of crystals was not observed.

EXAMPLE 10

(Use Example 8)

Physical properties of the liquid crystal composition of Composition Example 7 were as follows:

NI: 75.6, Δε: 24.6, Δn: 0.122, η: 38.4, Vth: 0.97

While this liquid crystal composition was allowed to stand in a freezer at –20° C., development of smectic phase or separation of crystals was not observed.

EXAMPLE 11
(Use Example 9)

Physical properties of the liquid crystal composition of Composition Example 8 were as follows:

NI: 91.1, $\Delta\epsilon$: 4.8, $\Delta n$: 0.118, $\eta$: 16.0, Vth: 2.36

While this liquid crystal composition was allowed to stand in a freezer at −20° C., development of smectic phase or separation of crystals was not observed.

EXAMPLE 12
(Use Example 10)

Physical properties of the liquid crystal composition of Composition Example 9 were as follows:

NI: 90.3, $\Delta\epsilon$: 28.7, $\Delta n$: 0.142, $\eta$: 40.6, Vth: 0.98

While this liquid crystal composition was allowed to stand in a freezer at −20° C., development of smectic phase or separation of crystals was not observed.

EXAMPLE 13
(Use Example 11)

Physical properties of the liquid crystal composition of Composition Example 10 were as follows:

NI: 61.3, $\Delta\epsilon$: 10.7, $\Delta n$: 0.118, $\eta$: 28.2, Vth: 1.30

While this liquid crystal composition was allowed to stand in a freezer at −20° C., development of smectic phase or separation of crystals was not observed.

EXAMPLE 14
(Use Example 12)

Physical properties of the liquid crystal composition of Composition Example 11 were as follows:

NI: 65.4, $\Delta\epsilon$: 7.7, $\Delta n$: 0.169, $\eta$: 25.4, Vth: 1.66

While this liquid crystal composition was allowed to stand in a freezer at −20° C., development of smectic phase or separation of crystals was not observed.

EXAMPLE 15
(Use Example 13)

Physical properties of the liquid crystal composition of Composition Example 12 were as follows:

NI: 101.3, $\Delta\epsilon$: 8.3, $\Delta n$: 0.135, $\eta$: 18.0, Vth: 2.08

While this liquid crystal composition was allowed to stand in a freezer at −20° C., development of smectic phase or separation of crystals was not observed.

EXAMPLE 16
(Use Example 14)

Physical properties of the liquid crystal composition of Composition Example 13 were as follows:

NI: 99.8, $\Delta\epsilon$: 7.4, $\Delta n$: 0.208, $\eta$: 15.6, Vth: 2.01

While this liquid crystal composition was allowed to stand in a freezer at −20° C., development of smectic phase or separation of crystals was not observed.

EXAMPLE 17
(Use Example 15)

Physical properties of the liquid crystal composition of Composition Example 14 were as follows:

NI: 80.0, $\Delta\epsilon$: 7.0, $\Delta n$: 0.130, $\eta$: 13.6, Vth: 2.00

While this liquid crystal composition was allowed to stand in a freezer at −20° C., development of smectic phase or separation of crystals was not observed.

EXAMPLE 18
(Use Example 16)

Physical properties of the liquid crystal composition of Composition Example 15 were as follows:

NI: 99.7, $\Delta\epsilon$: 5.7, $\Delta n$: 0.106, $\eta$: 21.4, Vth: 2.35

While this liquid crystal composition was allowed to stand in a freezer at −20° C., development of smectic phase or separation of crystals was not observed.

EXAMPLE 19
(Use Example 17)

Physical properties of the liquid crystal composition of Composition Example 16 were as follows:

NI: 80.9, $\Delta\epsilon$: 11.1, $\Delta n$: 0.148, $\eta$: 26.5, Vth: 1.70

While this liquid crystal composition was allowed to stand in a freezer at −20° C., development of smectic phase or separation of crystals was not observed.

EXAMPLE 20
(Use Example 18)

Physical properties of the liquid crystal composition of Composition Example 17 were as follows:

NI: 101.3, $\Delta\epsilon$: 6.3, $\Delta n$: 0.099, $\eta$: 27.4, Vth: 2.08, P: 79

While this liquid crystal composition was allowed to stand in a freezer at −20° C., development of smectic phase or separation of crystals was not observed.

EXAMPLE 21
(Use Example 19)

Physical properties of the liquid crystal composition of Composition Example 18 were as follows:

NI: 88.4, $\Delta\epsilon$: 3.9, $\Delta n$: 0.096, $\eta$: 20.2, Vth: 2.52

While this liquid crystal composition was allowed to stand in a freezer at −20° C., development of smectic phase or separation of crystals was not observed.

EXAMPLE 22
(Use Example 20)

Physical properties of the liquid crystal composition of Composition Example 19 were as follows:

NI: 85.9, $\Delta\epsilon$: 5.8, $\Delta n$: 0.116, $\eta$: 25.9, Vth: 1.99

While this liquid crystal composition was allowed to stand in a freezer at −20° C., development of smectic phase or separation of crystals was not observed.

EXAMPLE 23
(Use Example 21)

Physical properties of the liquid crystal composition of Composition Example 20 were as follows:

NI: 71.9, $\Delta\epsilon$: 9.1, $\Delta n$: 0.089, $\eta$: 25.8, Vth: 1.51, VHR: 97.1, 96.4, 95.9

While this liquid crystal composition was allowed to stand in a freezer at −20° C., development of smectic phase or separation of crystals was not observed.

EXAMPLE 24
(Use Example 22)

Physical properties of the liquid crystal composition of Composition Example 21 were as follows:

NI: 73.7, $\Delta\epsilon$: 13.7, $\Delta n$: 0.090, $\eta$: 35.3, Vth: 1.32

While this liquid crystal composition was allowed to stand in a freezer at −20° C., development of smectic phase or separation of crystals was not observed.

EXAMPLE 25
(Use Example 23)

Physical properties of the liquid crystal composition of Composition Example 22 were as follows:

NI: 90.1, $\Delta\epsilon$: 6.0, $\Delta n$: 0.136, $\eta$: 23.7, Vth: 2.11

While this liquid crystal composition was allowed to stand in a freezer at −20° C., development of smectic phase or separation of crystals was not observed.

EXAMPLE 26

(Use Example 24)

Physical properties of the liquid crystal composition of Composition Example 23 were as follows:

NI: 96.5, Δε: 9.4, Δn: 0.116, η: 34.9, Vth: 1.70

While this liquid crystal composition was allowed to stand in a freezer at −20° C., development of smectic phase or separation of crystals was not observed.

EXAMPLE 27

(Use Example 25)

Physical properties of the liquid crystal composition of Composition Example 24 were as follows:

NI: 83.8, Δε: 4.8, Δn: 0.093, η: 15.7, Vth: 2.35

While this liquid crystal composition was allowed to stand in a freezer at −20° C., development of smectic phase or separation of crystals was not observed.

EXAMPLE 28

(Use Example 26)

Physical properties of the liquid crystal composition of Composition Example 25 were as follows:

NI: 70.0, Δε: 8.9, Δn: 0.100, η: 27.3, Vth: 1.69

While this liquid crystal composition was allowed to stand in a freezer at −20° C., development of smectic phase or separation of crystals was not observed.

EXAMPLE 29

(Use Example 27)

Physical properties of the liquid crystal composition of Composition Example 26 were as follows:

NI: 89.6, Δε: 8.3, Δn: 0.137, η: 35.8, Vth: 1.79

While this liquid crystal composition was allowed to stand in a freezer at −20° C., development of smectic phase or separation of crystals was not observed.

EXAMPLE 30

(Use Example 28)

Physical properties of the liquid crystal composition of Composition Example 27 were as follows:

NI: 72.6, Δε: 5.0, Δn: 0.093, η: 17.8, Vth: 2.09

While this liquid crystal composition was allowed to stand in a freezer at −20° C., development of smectic phase or separation of crystals was not observed.

EXAMPLE 31

(Use Example 29)

Physical properties of the liquid crystal composition of Composition Example 28 were as follows:

NI: 101.5, Δε: 8.7, Δn: 0.122, η: 38.7, Vth: 1.71, VHR: 97.7, 96.6, 96.1

While this liquid crystal composition was allowed to stand in a freezer at −20° C., development of smectic phase or separation of crystals was not observed.

EXAMPLE 32

(Use Example 30)

Physical properties of the liquid crystal composition of Composition Example 29 were as follows:

NI: 95.7, Δε: 9.9, Δn: 0.136, η: 20.8, Vth: 1.95

While this liquid crystal composition was allowed to stand in a freezer at −20° C., development of smectic phase or separation of crystals was not observed.

EXAMPLE 33

(Use Example 31)

Physical properties of the liquid crystal composition of Composition Example 30 were as follows:

NI: 82.7, Δε: 12.0, Δn: 0.100, η: 33.4, Vth: 1.65

While this liquid crystal composition was allowed to stand in a freezer at −20° C, development of smectic phase or separation of crystals was not observed.

EXAMPLE 34

(Use Example 32)

Physical properties of the liquid crystal composition of composition Example 31 were as follows:

NI: 84.0, Δε: −3.5, Δn: 0.082

While this liquid crystal composition was allowed to stand in a freezer at −20° C., development of smectic phase or separation of crystals was not observed.

Liquid crystalline compounds of the present invention have an extremely high voltage holding ratio, are considerably small in its alteration caused by the change of temperature, and have a low threshold voltage and a high Δn. Further, liquid crystalline compounds having desired physical properties can be provided by selecting a proper substituent and bonding group in the liquid crystalline compounds of the present invention.

Industrial Applicability

Accordingly, novel liquid crystal compositions having an extremely high voltage holding ratio, being considerably small in its alteration by the change of temperature, having a suitable height of Δn and Δε, and being excellent in stability and miscibility with other liquid crystal materials can be provided by using the liquid crystalline compound of the present invention as component of liquid crystal compositions. Further, excellent liquid crystal display devices of in-plane-switching (IPS) mode or vertical alignment (VA) mode can be provided by using the liquid crystal composition.

What is claimed is:

1. A liquid crystalline compound expressed by the general formula (1)

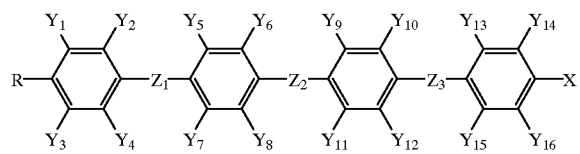

(1)

wherein R represents an alkyl group having 1 to 20 carbon atoms in which alkyl group any not-adjacent methylene group (—$CH_2$—) may be replaced by oxygen (—O—) atom; $Y_1$ to $Y_{16}$ independently represent hydrogen atom or fluorine atom, but at least three of them are fluorine atoms, provided that in no case three or more hydrogen atoms of one 1,4-phenylene group are replaced by fluorine atom; X represents a halogen atom or an alkyl group having 1 to 20 carbon atoms in which alkyl group any not-adjacent methylene group may be replaced by oxygen atom, and any hydrogen atom in the alkyl group may be replaced by fluorine atom; and $Z_1$, $Z_2$, and $Z_3$ independently represent —$(CH_2)_2$—, —$(CH_2)_4$—, —$CH_2O$—, —$OCH_2$—, —$(CH_2)_3O$—, —$O(CH_2)_3$—, or single bond; provided that when X=—OCF$_2$CF$_2$H, Z$_1$=Z$_3$=single bond, and Z$_2$=—(CH$_2$)$_2$—, in no case Y$_6$=Y$_{10}$=Y$_{12}$=F, and Y$_1$ to Y$_5$ =Y$_7$ to Y$_9$=Y$_{11}$=Y$_{13}$ to Y$_{16}$=H, Y$_2$=Y$_{10}$=Y$_{12}$=F, and Y$_1$=Y$_3$ to Y$_9$=Y$_{11}$=Y$_{13}$ to Y$_{16}$=H, or Y$_2$=Y$_4$=Y$_{10}$=Y$_{12}$=F, and Y$_1$=Y$_3$=Y$_5$ to Y$_9$=Y$_{11}$=Y$_{13}$ to Y$_{16}$=H.

2. The liquid crystalline compound according to claim 1 wherein X is a halogen atom, —CF$_3$—, —CF$_2$H, —CFH$_2$, —OCF$_3$, —OCF$_2$H, —OCF$_2$CH$_2$CF$_3$, —OCF$_2$CFHCF$_3$, an alkyl group having 1 to 20 carbon atoms, an alkoxy group having 1 to 20 carbon atoms, or an alkoxyalkyl group having 1 to 20 carbon atoms.

3. A liquid crystal composition comprising at least two components, at least one of which is a liquid crystalline compound defined in claim 1 or 2.

4. A liquid crystal composition comprising, as a first component, at least one compound defined in claim 1 or 2, as a second component, at least one compound selected from the group consisting of the compounds expressed by the general formulas (2), (3), and (4)

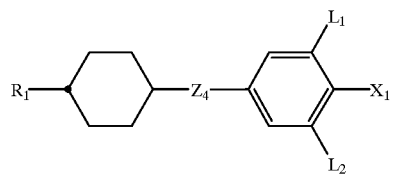

(2)

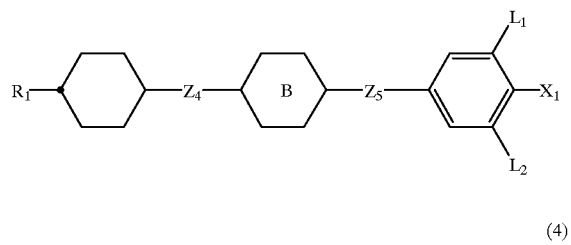

(3)

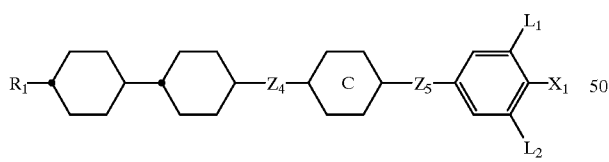

(4)

wherein R$_1$ represents an alkyl group having 1 to 10 carbon atoms. in which alkyl group any not-adjacent methylene group may be replaced by oxygen atom or —CH=CH—, and any hydrogen atom in the alkyl group may be replaced by fluorine atom; X$_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; L, and L$_2$ independently represent hydrogen atom or fluorine atom; Z$_4$ and Z$_5$ independently represent 1,2-ethylene group, 1,4-butylene group, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; ring C represents trans-1,4-cyclohexylene, or 1,4-phenylene in which hydrogen atom may be replaced by fluorine atom; and any atom which constitutes these compounds may be replaced by its isotope, and optionally, as a third component, at least one optically active compound.

5. A liquid crystal composition comprising, as a first component, at least one compound defined in claim 1 or 2, as a second component, at least one compound selected from the group consisting of the compounds expressed by the general formulas (5) and (6)

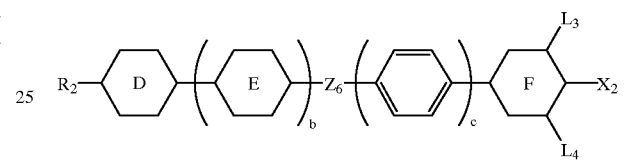

(5)

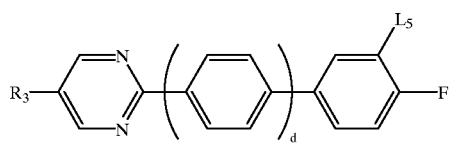

(6)

wherein R$_2$ and R$_3$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; X$_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; Z$_6$ represents 1,2-ethylene group, —COO—, or single bond; L$_3$, L$_4$, and L$_5$ independently represent hydrogen atom or fluorine atom; b, c, and d are independently 0 or 1; and any atom which constitutes these compounds may be replaced by its isotope, and optionally, as a third component, at least one optically active compound.

6. A liquid crystal composition comprising, as a first component, at least one compound defined in claim 1 or 2, as a second component, at least one compound selected from the group consisting of the compounds expressed by the general formulas (2), (3), and (4)

(2)
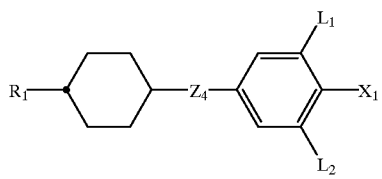

(3)
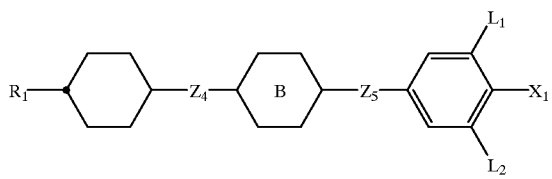

(4)
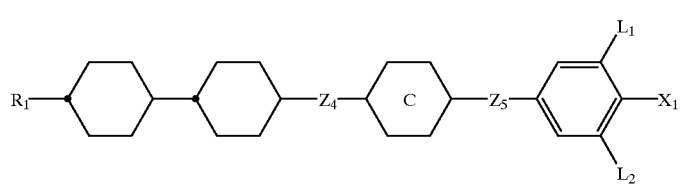

wherein $R_1$ represents an alkyl group having 1 to 10 carbon atoms. in which alkyl group any not-adjacent methylene group may be replaced by oxygen atom or —CH=CH—, and any hydrogen atom in the alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently represent hydrogen atom or fluorine atom; $Z_4$ and $Z_5$ independently represent 1,2-ethylene group, 1,4-butylene group, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; ring C represents trans-1,4-cyclohexylene, or 1,4-phenylene in which hydrogen atom may be replaced by fluorine atom; and any atom which constitutes these compounds may be replaced by its isotope, as a third component, at least one compound selected from the group consisting of the compounds expressed by the general formulas (7), (8), and (9)

wherein $R_4$ and $R_5$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring G, ring I, and ring J independently represent trans-1,4-cyclohexylene or pyrimidine-2,5-diyl, or 1,4-phenylene in which hydrogen atom may be replaced by fluorine atom; $Z_7$ and $Z_8$ independently represent —C≡C—, —COO—, —CH$_2$CH$_2$—, —CH=CH—, or single bond; and any atom which constitutes these compounds may be replaced by its isotope, and optionally, as a fourth component, at least one optically active compound.

7. A liquid crystal composition comprising, as a first component, at least one compound defined in claim 1 or 2, as a second component, at least one compound selected from the group consisting of the compounds expressed by the general formulas (5) and (6), (7)
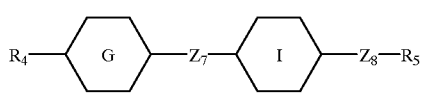

(8)
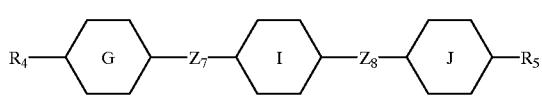

(9)
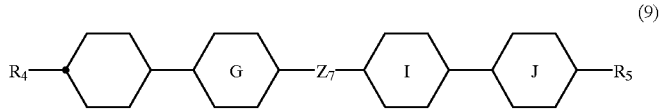

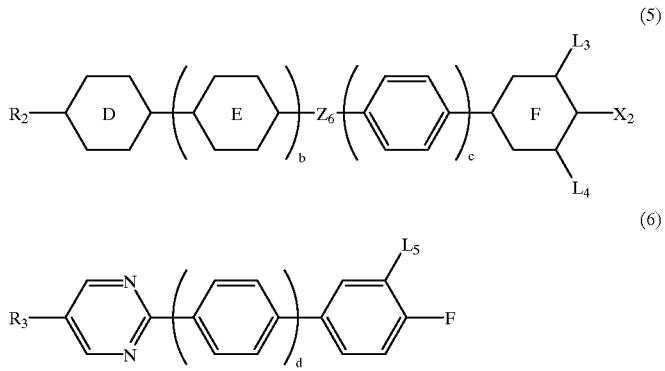

(5)

(6)

wherein $R_2$ and $R_3$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; $Z_6$ represents 1,2-ethylene group, —COO—, or single bond; $L_3$, $L_4$, and $L_5$ independently represent hydrogen atom or fluorine atom; b, c, and d are independently 0 or 1; and any atom which constitutes these compounds may be replaced by its isotope, as a third component, at least one compound selected from the group consisting of the compounds expressed by general formulas (7), (8), and (9)

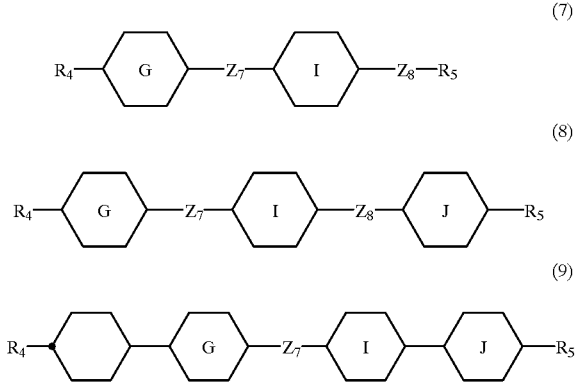

wherein $R_4$ and $R_5$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring G, ring I, and ring J independently represent trans- 1,4-cyclohexylene or pyrimidine-2,5-diyl, or 1,4-phenylene in which hydrogen atom may be replaced by fluorine atom; $Z_7$ and $Z_8$ independently represent —C≡C—, —COO—, —CH$_2$CH$_2$—, —CH=CH—, or single bond; and any atom which constitutes these compounds may be replaced by its isotope, and optionally, as a fourth component, at least one optically active compound.

8. A liquid crystal composition comprising, as a first component, at least one compound defined in claim 1 or 2, as a second component, at least one compound selected from the group consisting of the compounds expressed by the general formulas (10), (11), and (12)

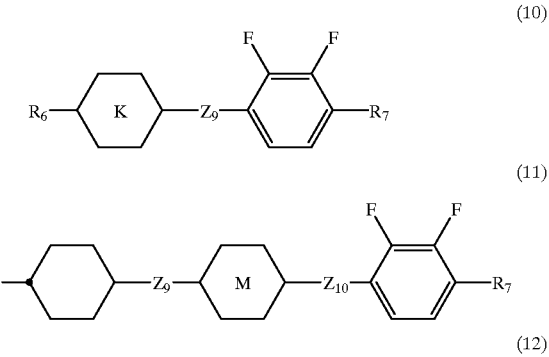

wherein $R_6$ and $R_7$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring K and ring M independently represent trans-1,4-cyclohexylene or 1,4-phenylene; $L_6$ and $L_7$ independently represent hydrogen atom or fluorine atom, but in no case $L_6$ and $L_7$ simultaneously represent hydrogen atom; $Z_9$ and $Z_{10}$ independently represent —CH$_2$CH$_2$—, —COO—, or single bond; and any atom which constitutes these compounds may be replaced by its isotope, and optionally, as a third component, at least one optically active compound.

9. A liquid crystal composition comprising, as a first component, at least one compound defined in claim 1 or 2, as a second component, at least one compound selected from the group consisting of the compounds expressed by the general formulas (7), (8), and (9)

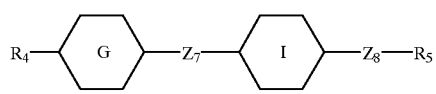
(7)

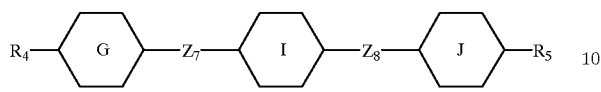
(8)

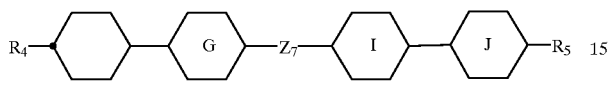
(9)

wherein $R_4$ and $R_5$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring G, ring I, and ring J independently represent trans-1,4-cyclohexylene or pyrimidine-2,5-diyl, or 1,4-phenylene in which hydrogen atom may be replaced by fluorine atom; $Z_7$ and $Z_8$ independently represent —C≡C—, —COO—, —CH$_2$CH$_2$—, —CH=CH—, or single bond; and any atom which constitutes these compounds may be replaced by its isotope, as a third component, at least one compound selected from the group consisting of the compounds expressed by the general formulas (10), (11), and (12)

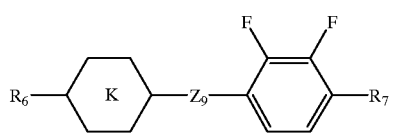
(10)

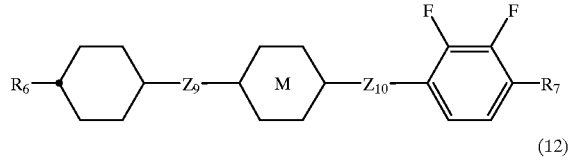
(11)

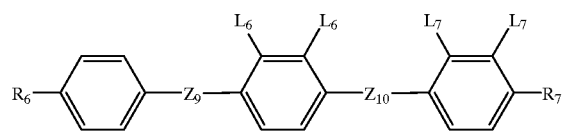
(12)

wherein $R_6$ and $R_7$ independently represent an alkyl group having 1 to 10 carbon atoms in which alkyl group any not-adjacent methylene group may be-replaced by oxygen atom or —CH=CH—, and any hydrogen atom in the alkyl group may be replaced by fluorine atom; ring K and ring M independently represent trans-1,4-cyclohexylene or 1,4-phenylene; $L_6$ and $L_7$ independently represent hydrogen atom or fluorine atom, but in no case $L_6$ and $L_7$ simultaneously represent hydrogen atom; $Z_9$ and $Z_{10}$ independently represent —CH$_2$CH$_2$—, —COO—, or single bond; and any atom which constitutes these compounds may be replaced by its isotope, and optionally, as fourth component, at least one optically active compound.

10. A liquid crystal composition comprising, as a first component, at least one compound defined in claim 1 or 2, as a second component, at least one compound selected from the group consisting of the compounds expressed by the general formulas (2), (3), and (4)

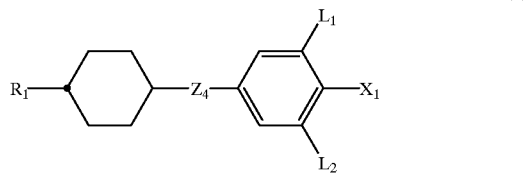
(2)

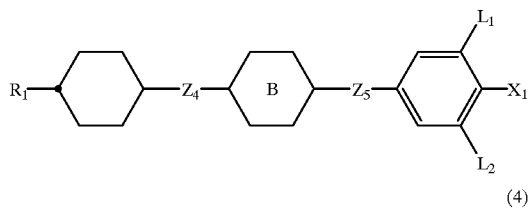
(3)

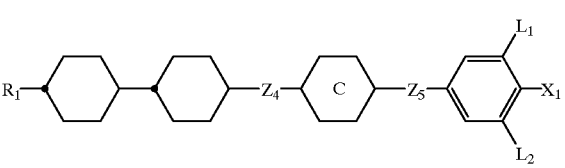
(4)

wherein $R_1$ represents an alkyl group having 1 to 10 carbon atoms. in which alkyl group any not-adjacent methylene group may be replaced by oxygen atom or —CH=CH—, and any hydrogen atom in the alkyl group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ independently represent hydrogen atom or fluorine atom; $Z_4$ and $Z_5$ independently represent 1,2-ethylene group, 1,4-butylene group, —COO—, —CF$_2$O—, —OCF$_2$—, —CH=CH—, or single bond; ring B represents trans-1,4-cyclohexylene or 1,3-dioxane-2,5-diyl, or 1,4-phenylene in which hydrogen atom may be replaced by fluorine atom; ring c represents trans-1,4-cyclohexylene, or 1,4-phenylene in which hydrogen atom may be replaced by fluorine atom; and any-atom which constitutes these compounds may be replaced by its isotope, as a third component, at least one compound selected from the group consisting of the compounds expressed by the general formulas (5) and (6)

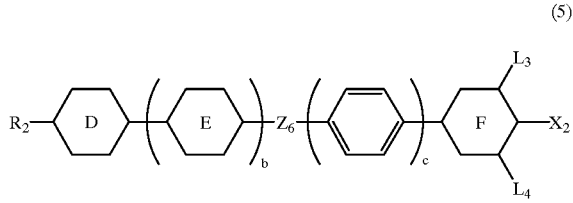
(5)

(6)

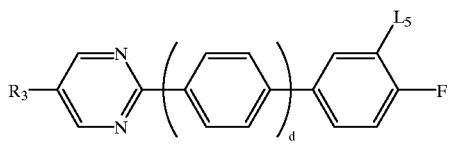

(8)

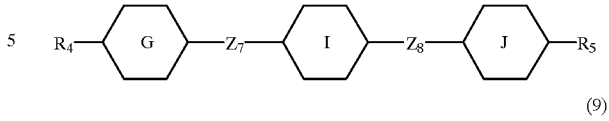

(9)

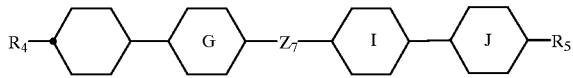

wherein $R_2$ and $R_3$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; $X_2$ represents —CN or —C≡C—CN; ring D represents trans-1,4-cyclohexylene, 1,4-phenylene, 1,3-dioxane-2,5-diyl, or pyrimidine-2,5-diyl; ring E represents trans-1,4-cyclohexylene or pyrimidine-2,5-diyl, or 1,4-phenylene in which hydrogen atom may be replaced by fluorine atom; ring F represents trans-1,4-cyclohexylene or 1,4-phenylene; $Z_6$ represents 1,2-ethylene group, —COO—, or single bond; $L_3$, $L_4$, and $L_5$ independently represent hydrogen atom or fluorine atom; b, c, and d are independently 0 or 1; and any atom which constitutes these compounds may be replaced by its isotope, as a fourth component, at least one compound selected from the group consisting of the compounds expressed by the general formulas (7), (8), and (9)

(7)

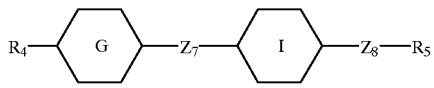

wherein $R_4$ and $R_5$ independently represent an alkyl group having 1 to 10 carbon atoms in which alkyl group any not-adjacent methylene group may be replaced by oxygen atom or —CH=CH—, and any hydrogen atom in the alkyl group may be replaced by fluorine atom; ring G, ring I, and ring J independently represent trans-1,4-cyclohexylene or pyrimidine-2,5-diyl, or 1,4-phenylene in which hydrogen atom may be replaced by fluorine atom; $Z_7$ and $Z_8$ independently represent —C≡C—, —COO—, —CH$_2$CH$_2$—, —CH=CH—, or single bond; and any atom which constitutes these compounds may be replaced by its isotope, and optionally, as a fifth component, at least one optically active compound.

11. A liquid crystal display device comprising the liquid crystal composition defined in claim 3.

* * * * *